US012186553B2

(12) United States Patent
Schmidt et al.

(10) Patent No.: US 12,186,553 B2
(45) Date of Patent: Jan. 7, 2025

(54) ELECTRICAL STIMULATION FOR CANCER TREATMENT WITH INTERNAL AND EXTERNAL ELECTRODES

(71) Applicant: Boston Scientific Scimed, Inc., Maple Grove, MN (US)

(72) Inventors: Brian L. Schmidt, White Bear Lake, MN (US); Devon N. Arnholt, Shoreview, MN (US); Benjamin Keith Stein, Shoreview, MN (US); Keith R. Maile, New Brighton, MN (US); William J. Linder, Golden Valley, MN (US); Ron A. Balczewski, Bloomington, MN (US); Jacob M. Ludwig, Isanti, MN (US); Aleksandra Kharam, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/123,776

(22) Filed: Mar. 20, 2023

(65) Prior Publication Data

US 2023/0330416 A1    Oct. 19, 2023

Related U.S. Application Data

(63) Continuation of application No. 16/855,421, filed on Apr. 22, 2020, now Pat. No. 11,607,542.
(Continued)

(51) Int. Cl.
*A61N 1/36* (2006.01)
*A61N 1/04* (2006.01)
(Continued)

(52) U.S. Cl.
CPC ....... *A61N 1/36002* (2017.08); *A61N 1/0408* (2013.01); *A61N 1/05* (2013.01);
(Continued)

(58) Field of Classification Search
CPC .................................................. A61N 1/36002
See application file for complete search history.

(56) References Cited

U.S. PATENT DOCUMENTS

| 4,016,886 A | 4/1977 | Doss et al. |
| 5,099,838 A | 3/1992 | Bardy |

(Continued)

FOREIGN PATENT DOCUMENTS

| CN | 202844368 | 4/2013 |
| JP | 2011030734 | 2/2011 |

(Continued)

OTHER PUBLICATIONS

"Decision of Rejection," for Japanese Patent Application No. 2021-562797 mailed May 16, 2023 (10 pages), with English translation.
(Continued)

*Primary Examiner* — Michael W Kahelin
(74) *Attorney, Agent, or Firm* — Pauly, DeVries Smith & Deffner LLC

(57) ABSTRACT

Embodiments herein relate to medical devices and methods for using the same to treat cancerous tumors within a bodily tissue. A medical device system is included having at least one electric field generating circuit configured to generate one or more electric fields; control circuitry in communication with the electric field generating circuit, the control circuitry configured to control delivery of the one or more electric fields from the at least one electric field generating circuit; and two or more electrodes to deliver the electric fields to the site of a cancerous tumor within a patient. At least one electrode can be configured to be implanted. At
(Continued)

least one electrode can be configured to be external. The control circuitry can cause the electric field generating circuit to generate one or more electric fields at frequencies selected from a range of between 10 kHz to 1 MHz.

8 Claims, 14 Drawing Sheets

Related U.S. Application Data

(60) Provisional application No. 62/837,401, filed on Apr. 23, 2019.

(51) Int. Cl.
*A61N 1/05* (2006.01)
*A61N 1/378* (2006.01)

(52) U.S. Cl.
CPC ..... *A61N 1/36017* (2013.01); *A61N 1/36034* (2017.08); *A61N 1/3787* (2013.01)

(56) References Cited

U.S. PATENT DOCUMENTS

| | | |
|---|---|---|
| 5,113,869 A | 5/1992 | Nappholz et al. |
| 5,324,328 A | 6/1994 | Li et al. |
| 5,397,342 A | 3/1995 | Heil et al. |
| 5,458,597 A | 10/1995 | Edwards et al. |
| 5,582,609 A | 12/1996 | Swanson et al. |
| 5,630,426 A | 5/1997 | Eggers et al. |
| 5,662,698 A | 9/1997 | Altman et al. |
| 5,834,051 A | 11/1998 | Woloszko et al. |
| 5,871,530 A | 2/1999 | Williams et al. |
| 6,006,755 A | 12/1999 | Edwards |
| 6,366,808 B1 | 4/2002 | Schroeppel et al. |
| 6,673,623 B1 | 1/2004 | Huberman |
| 6,868,289 B2 | 3/2005 | Palti |
| 6,920,361 B2 | 7/2005 | Williams |
| 7,162,310 B2 | 1/2007 | Doan |
| 7,449,021 B2 | 11/2008 | Underwood et al. |
| 7,524,274 B2 | 4/2009 | Patrick et al. |
| 7,565,205 B2 | 7/2009 | Palti |
| 7,632,235 B1 | 12/2009 | Karicherla et al. |
| 7,656,205 B2 | 2/2010 | Chen et al. |
| 7,715,921 B2 | 5/2010 | Palti |
| 7,720,549 B2 | 5/2010 | Schroeppel et al. |
| 7,805,201 B2 | 9/2010 | Palti |
| 7,809,441 B2 | 10/2010 | Kane et al. |
| 7,890,183 B2 | 2/2011 | Palti et al. |
| 7,917,227 B2 | 3/2011 | Palti |
| 8,002,821 B2 | 8/2011 | Stinson |
| 8,019,414 B2 | 9/2011 | Palti |
| 8,170,648 B2 | 5/2012 | Field et al. |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,483,821 B2 | 7/2013 | Averina et al. |
| 8,500,713 B2 | 8/2013 | Ferek-Petric |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 8,805,466 B2 | 8/2014 | Salahieh et al. |
| 8,956,352 B2 | 2/2015 | Mauch et al. |
| 9,005,100 B2 | 4/2015 | Gnanashanmugam et al. |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,179,974 B2 | 11/2015 | Ku et al. |
| 9,248,278 B2 | 2/2016 | Crosby et al. |
| 9,283,383 B2 | 3/2016 | Osypka |
| 9,308,039 B2 | 4/2016 | Azure |
| 9,387,323 B2 | 7/2016 | Fleischhacker et al. |
| 9,427,278 B2 | 8/2016 | Swanson |
| 9,440,068 B2 | 9/2016 | Palti et al. |
| 9,474,486 B2 | 10/2016 | Eliason et al. |
| 9,526,911 B1 | 12/2016 | Azure et al. |
| 9,630,022 B2 | 4/2017 | Bourke et al. |
| 9,655,669 B2 | 5/2017 | Palti et al. |
| 9,750,934 B2 | 9/2017 | Palti et al. |
| 9,833,617 B2 | 12/2017 | Travers et al. |
| 9,877,781 B2 | 1/2018 | Grasse et al. |
| 9,910,453 B2 | 3/2018 | Wasserman et al. |
| 10,029,117 B2 | 7/2018 | Bourke |
| 10,238,862 B2 | 3/2019 | Cook et al. |
| 10,265,530 B1 | 4/2019 | Perryman et al. |
| 10,376,177 B2 | 8/2019 | Valvano et al. |
| 10,471,254 B2 | 11/2019 | Sano et al. |
| 11,191,956 B2 | 12/2021 | Giladi et al. |
| 11,331,493 B2 | 5/2022 | Pivonka et al. |
| 11,338,135 B2 | 5/2022 | Schmidt et al. |
| 11,420,049 B2* | 8/2022 | Schmidt ........ A61N 1/05 |
| 11,607,542 B2 | 3/2023 | Schmidt et al. |
| 11,691,006 B2* | 7/2023 | Schmidt ...... A61N 1/36002 607/62 |
| 11,712,561 B2 | 8/2023 | Schmidt et al. |
| 11,850,422 B2 | 12/2023 | Schmidt et al. |
| 11,883,655 B2 | 1/2024 | Srivastava et al. |
| 2001/0044643 A1 | 11/2001 | Litovitz |
| 2002/0026183 A1 | 2/2002 | Simpson |
| 2002/0049485 A1 | 4/2002 | Smits |
| 2002/0065544 A1 | 5/2002 | Smits |
| 2003/0020416 A1 | 1/2003 | Kobayashi |
| 2003/0069623 A1 | 4/2003 | Stypulkowski |
| 2003/0204161 A1 | 10/2003 | Ferek-Petric |
| 2004/0010290 A1 | 1/2004 | Schroeppel et al. |
| 2004/0010303 A1 | 1/2004 | Bolea et al. |
| 2004/0147969 A1 | 7/2004 | Mann et al. |
| 2004/0158288 A1 | 8/2004 | Keisari et al. |
| 2004/0162600 A1 | 8/2004 | Williams |
| 2004/0176804 A1 | 9/2004 | Palti |
| 2004/0215235 A1 | 10/2004 | Jackson et al. |
| 2004/0215296 A1 | 10/2004 | Ganz et al. |
| 2005/0004507 A1 | 1/2005 | Schroeppel et al. |
| 2005/0043894 A1 | 2/2005 | Fernandez |
| 2005/0096584 A1 | 5/2005 | Ferek-Petric |
| 2005/0209642 A1 | 9/2005 | Palti |
| 2005/0222623 A1 | 10/2005 | Kroll et al. |
| 2005/0222646 A1 | 10/2005 | Kroll et al. |
| 2005/0240173 A1 | 10/2005 | Palti |
| 2005/0288730 A1 | 12/2005 | Deem et al. |
| 2005/0288761 A1 | 12/2005 | Brabec et al. |
| 2006/0024802 A1 | 2/2006 | Muller et al. |
| 2006/0149341 A1 | 7/2006 | Palti |
| 2006/0190053 A1 | 8/2006 | Dobak |
| 2006/0259092 A1 | 11/2006 | Spadgenske et al. |
| 2006/0259099 A1 | 11/2006 | Goetz et al. |
| 2006/0282122 A1 | 12/2006 | Palti |
| 2006/0282126 A1 | 12/2006 | Fischbach et al. |
| 2007/0033660 A1 | 2/2007 | Palti |
| 2007/0135861 A1 | 6/2007 | Wallace et al. |
| 2007/0179550 A1 | 8/2007 | Dennis et al. |
| 2007/0225766 A1 | 9/2007 | Palti |
| 2007/0239213 A1 | 10/2007 | Palti |
| 2007/0239244 A1 | 10/2007 | Morgan et al. |
| 2007/0270675 A1 | 11/2007 | Kane et al. |
| 2007/0270916 A1 | 11/2007 | Fischell et al. |
| 2008/0058669 A1 | 3/2008 | Kroll |
| 2008/0058887 A1 | 3/2008 | Griffin et al. |
| 2008/0071350 A1 | 3/2008 | Stinson et al. |
| 2008/0086073 A1 | 4/2008 | McDaniel |
| 2008/0097424 A1 | 4/2008 | Wizeman et al. |
| 2008/0172116 A1 | 7/2008 | Mrva et al. |
| 2008/0195227 A1 | 8/2008 | Boling et al. |
| 2008/0208271 A1 | 8/2008 | Sih et al. |
| 2008/0275524 A1 | 11/2008 | Furness et al. |
| 2009/0076500 A1 | 3/2009 | Azure et al. |

(56) References Cited

U.S. PATENT DOCUMENTS

| | | |
|---|---|---|
| 2009/0192381 A1 | 7/2009 | Brockway et al. |
| 2009/0234211 A1 | 9/2009 | Li et al. |
| 2010/0016936 A1 | 1/2010 | Stevenson et al. |
| 2010/0168820 A1 | 7/2010 | Maniak et al. |
| 2010/0198298 A1 | 8/2010 | Schulman et al. |
| 2010/0217356 A1 | 8/2010 | Bikson et al. |
| 2010/0261994 A1 | 10/2010 | Davalos et al. |
| 2010/0298895 A1 | 11/2010 | Ghaffari et al. |
| 2010/0331938 A1 | 12/2010 | Sommer et al. |
| 2011/0071608 A1 | 3/2011 | Fleischhacker et al. |
| 2011/0125215 A1 | 5/2011 | Goetz et al. |
| 2011/0137229 A1 | 6/2011 | Palti et al. |
| 2011/0224665 A1 | 9/2011 | Crosby et al. |
| 2011/0238057 A1 | 9/2011 | Moss et al. |
| 2011/0306878 A1 | 12/2011 | Desimone et al. |
| 2012/0035616 A1 | 2/2012 | Olsen et al. |
| 2012/0130444 A1 | 5/2012 | Wei et al. |
| 2012/0158072 A1 | 6/2012 | Venook et al. |
| 2012/0158122 A1 | 6/2012 | Mattson et al. |
| 2012/0203307 A1 | 8/2012 | Schroeppel et al. |
| 2012/0232615 A1 | 9/2012 | Barolat et al. |
| 2012/0283726 A1 | 11/2012 | Palti |
| 2013/0023946 A1 | 1/2013 | Valvano et al. |
| 2013/0165916 A1 | 6/2013 | Mathur et al. |
| 2013/0204068 A1 | 8/2013 | Gnanashanmugam et al. |
| 2013/0261706 A1 | 10/2013 | Mirro et al. |
| 2013/0261711 A1 | 10/2013 | Sivo |
| 2013/0289649 A1 | 10/2013 | Averina et al. |
| 2013/0289664 A1 | 10/2013 | Johanek |
| 2013/0310898 A1 | 11/2013 | Ollivier et al. |
| 2014/0005753 A1 | 1/2014 | Carbunaru |
| 2014/0052227 A1 | 2/2014 | Wahlstrand et al. |
| 2014/0107511 A1 | 4/2014 | Banet et al. |
| 2014/0142670 A1 | 5/2014 | Radhakrishnan et al. |
| 2014/0276781 A1 | 9/2014 | Beani et al. |
| 2014/0276811 A1 | 9/2014 | Koblish et al. |
| 2014/0350541 A1 | 11/2014 | Hill et al. |
| 2014/0350653 A1 | 11/2014 | Shiroff et al. |
| 2015/0005804 A1 | 1/2015 | Franano et al. |
| 2015/0066024 A1* | 3/2015 | Azure ............... A61B 18/1492 606/41 |
| 2015/0119952 A1 | 4/2015 | Sharma et al. |
| 2015/0134022 A1 | 5/2015 | Lee et al. |
| 2015/0180161 A1 | 6/2015 | Olson et al. |
| 2015/0182282 A1 | 7/2015 | Zemel et al. |
| 2015/0320995 A1 | 11/2015 | Nazareth et al. |
| 2015/0374992 A1 | 12/2015 | Crosby et al. |
| 2016/0022986 A1 | 1/2016 | Travers et al. |
| 2016/0029960 A1 | 2/2016 | Toth et al. |
| 2016/0068598 A1 | 3/2016 | Yan et al. |
| 2016/0082258 A1 | 3/2016 | Kramer et al. |
| 2016/0121106 A1 | 5/2016 | Marshall et al. |
| 2016/0128767 A1 | 5/2016 | Azamian et al. |
| 2016/0129276 A1 | 5/2016 | Fried et al. |
| 2016/0250476 A1 | 9/2016 | Kaemmerer et al. |
| 2016/0250483 A1 | 9/2016 | Klimovitch et al. |
| 2016/0331459 A1 | 11/2016 | Townley et al. |
| 2016/0346536 A1 | 12/2016 | Palti et al. |
| 2017/0007310 A1 | 1/2017 | Rajagopalan et al. |
| 2017/0035496 A1 | 2/2017 | Nagale et al. |
| 2017/0049514 A1 | 2/2017 | Cosman |
| 2017/0065339 A1 | 3/2017 | Mickelsen |
| 2017/0105793 A1 | 4/2017 | Cao et al. |
| 2017/0120041 A1 | 5/2017 | Wenger et al. |
| 2017/0173340 A1 | 6/2017 | Gupte et al. |
| 2017/0189098 A1 | 7/2017 | Azure et al. |
| 2017/0215939 A1 | 8/2017 | Palti et al. |
| 2017/0231694 A1 | 8/2017 | Mathur et al. |
| 2017/0251976 A1 | 9/2017 | Schouenborg |
| 2017/0266371 A1 | 9/2017 | Leonhardt et al. |
| 2017/0281934 A1 | 10/2017 | Giladi et al. |
| 2017/0281955 A1 | 10/2017 | Maile et al. |
| 2017/0312501 A1 | 11/2017 | Bornzin et al. |
| 2017/0333702 A1 | 11/2017 | Barner |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0021563 A1 | 1/2018 | Van De Stolpe et al. |
| 2018/0050200 A1 | 2/2018 | Wasserman et al. |
| 2018/0110978 A1 | 4/2018 | Beebe et al. |
| 2018/0154142 A1 | 6/2018 | Guo et al. |
| 2018/0221088 A1 | 8/2018 | Govari et al. |
| 2018/0246079 A1 | 8/2018 | Wang et al. |
| 2018/0256906 A1 | 9/2018 | Pivonka et al. |
| 2018/0289954 A1 | 10/2018 | Hebb et al. |
| 2019/0008555 A1 | 1/2019 | O'Mahony |
| 2019/0117962 A1 | 4/2019 | Chiang et al. |
| 2019/0117969 A1* | 4/2019 | Schmidt ............... A61N 1/0424 |
| 2019/0117970 A1* | 4/2019 | Schmidt ............... A61B 18/14 |
| 2019/0117971 A1* | 4/2019 | Schmidt ............... A61N 1/0424 |
| 2019/0117972 A1* | 4/2019 | Schmidt ............... A61B 18/18 |
| 2019/0117973 A1* | 4/2019 | Schmidt ............... A61N 1/36031 |
| 2019/0262605 A1* | 8/2019 | Babakhani ......... A61N 1/37205 |
| 2019/0321624 A1 | 10/2019 | De Kock et al. |
| 2020/0061385 A1 | 2/2020 | Schwarz et al. |
| 2020/0197086 A1 | 6/2020 | Azamian et al. |
| 2021/0339015 A1 | 11/2021 | Dinsmoor et al. |
| 2022/0288388 A1 | 9/2022 | Rondoni et al. |
| 2023/0218894 A1 | 7/2023 | Arnholt et al. |
| 2024/0024670 A1 | 1/2024 | Schmidt et al. |
| 2024/0115856 A1 | 4/2024 | Schmidt et al. |
| 2024/0226547 A1 | 7/2024 | Schmidt et al. |

FOREIGN PATENT DOCUMENTS

| | | |
|---|---|---|
| WO | 9639966 | 12/1996 |
| WO | 2023137008 | 7/2023 |

OTHER PUBLICATIONS

"Final Office Action," for U.S. Appl. No. 16/167,140 mailed May 24, 2023 (41 pages).

"Final Office Action," for U.S. Appl. No. 16/850,728 mailed Jun. 26, 2023 (26 pages).

"Response to Final Rejection," mailed Mar. 6, 2023 for U.S. Appl. No. 16/167,087, submitted via EFS-Web on Jun. 6, 2023, 10 pages.

"Response to Final Rejection," mailed on Mar. 7, 2023 for U.S. Appl. No. 16/166,957, submitted via EFS-Web on Jun. 7, 2023, 18 pages.

"Response to Non-Final Rejection," mailed on Mar. 23, 2023 for U.S. Appl. No. 16/167,079, submitted via EFS-Web on Jun. 23, 2023, 12 pages.

"Second Office Action," for Japanese Patent Application No. 2021-562798 mailed May 9, 2023 (11 pages) with English translation.

"Third Office Action," for Chinese Patent Application No. 201880068897.8 mailed Jun. 9, 2023 (10 pages) with English Summary.

"Communication Pursuant to Article 94(3) EPC," for European Patent Application No. 18801138.1 mailed Jul. 7, 2023 (5 pages).

"Office Action," for Canadian Patent Application No. 3,079,289 mailed Jul. 6, 2023 (3 pages).

"Office Action," for Japanese Patent Application No. 2021-562972 mailed May 5, 2023 (12 pages), with English translation.

"Response to Communication Pursuant to Article 94(3) EPC," for European Patent Application No. 20724333.8 filed Jul. 25, 2023 (28 pages).

"Response to Final Rejection," mailed on May 3, 2023, for U.S. Appl. No. 16/855,433, submitted via EFS-Web on Aug. 2, 2023, 10 pages.

"Second Office Action," for Japanese Patent Application No. 2021-562966 mailed Jun. 13, 2023 (9 pages), with English translation.

"Decision of Rejection," for Japanese Patent Application No. 2021-562972 mailed Sep. 5, 2023 (10 pages) with English Translation.

"Final Office Action," for U.S. Appl. No. 16/167,079 mailed Sep. 14, 2023 (33 pages).

"Fourth Office Action," for Chinese Patent Application No. 201880068897.8 mailed Oct. 17, 2023 (13 pages) with English Summary.

(56) References Cited

OTHER PUBLICATIONS

"International Preliminary Report on Patentability," for PCT Application No. PCT/US2022/021161 mailed Oct. 5, 2023 (9 pages).
"Non-Final Office Action," for U.S. Appl. No. 16/166,957 mailed Nov. 14, 2023 (39 pages).
"Non-Final Office Action," for U.S. Appl. No. 16/167,087 mailed Sep. 19, 2023 (38 pages).
"Non-Final Office Action," for U.S. Appl. No. 16/167,140 mailed Oct. 11, 2023 (32 pages).
"Notice of Allowance," for U.S. Appl. No. 16/855,433 mailed Aug. 23, 2023 (6 pages).
"Notice of Allowance," for U.S. Appl. No. 17/182,436 mailed Sep. 15, 2023 (17 pages).
"Office Action," for Japanese Patent Application No. 2021-562798 mailed Aug. 22, 2023 (4 pages) with English translation.
"Response to Communication Pursuant to Article 94(3) EPC," for European Patent Application No. 18801138.1 filed Nov. 16, 2023 (76 pages).
"Response to Final Office Action," mailed May 24, 2023, and Advisory Action mailed Sep. 20, 2023, for U.S. Appl. No. 16/167,140, submitted via EFS-Web on Sep. 25, 2023, 12 pages.
"Response to Final Rejection," mailed on Jun. 26, 2023 for U.S. Appl. No. 16/850,728, submitted via EFS-Web on Sep. 26, 2023, 11 pages.
"Response to Final Rejection," mailed on May 19, 2023, for U.S. Appl. No. 17/182,436, submitted via EFS-Web on Aug. 21, 2023, 14 pages.
"Response to Final Rejection," mailed on May 24, 2023, for U.S. Appl. No. 16/167,140, submitted via EFS-Web on Aug. 24, 2023, 11 pages.
"Response to Office Action," for Canadian Patent Application No. 3,079,289 filed Nov. 3, 2023 (13 pages).
"Summons to Attend Oral Proceedings," for European Patent Application No. 18801136.5 mailed Sep. 12, 2023 (13 pages).
"Supplemental Response to," Final Rejection mailed on Mar. 6, 2023, for U.S. Appl. No. 16/167,087, submitted via EFS-Web on Aug. 31, 2023, 7 pages.
"Zenchi Examination Report," for Japanese Patent Application No. 2021-562795 mailed Aug. 2, 2023 (9 pages) with English Summary.
"Decision of Rejection," for Japanese Patent Application No. 2021-562795 mailed Mar. 28, 2023 (6 pages) with English translation.
"Final Office Action," for U.S. Appl. No. 16/855,433 mailed May 3, 2023 (25 pages).
"Final Office Action," for U.S. Appl. No. 17/182,436 mailed May 19, 2023 (22 pages).
"First Office Action," for Chinese Patent Application No. 201880068852.0 mailed Mar. 15, 2023 (9 pages).
"First Office Action," for Chinese Patent Application No. 201880078118.2 mailed Mar. 27, 2023 (17 pages) with English translation.
"International Search Report and Written Opinion," for PCT Application No. PCT/US2023/010469 mailed Apr. 12, 2023 (19 pages).
"Non-Final Office Action," for U.S. Appl. No. 16/167,079 mailed Mar. 23, 2023 (40 pages).
"Response to Communication Pursuant to Article 94(3) EPC," for European Patent Application No. 18800411.3 filed May 2, 2023 (11 pages).
"Response to Non-Final Rejection," mailed on Jan. 24, 2023 for U.S. Appl. No. 16/850,728, submitted via EFS-Web on Apr. 20, 2023, 8 pages.
"Response to Office Action," for Canadian Patent Application No. 3,079,289 filed Mar. 24, 2023 (18 pages).
"Second Office Action," for Chinese Patent Application No. 201880068897.8 mailed Feb. 27, 2023 (9 pages) with English Summary.
"Extended European Search Report," for European Patent Application No. 24171875.8 mailed Jul. 16, 2024 (8 pages).
"Final Office Action," for U.S. Appl. No. 17/698,516 mailed Aug. 19, 2024 (25 pages).
"Final Rejection Action," for Chinese Patent Application No. 201880068852.0 mailed Jun. 7, 2024 (16 pages) with English Summary.
"International Preliminary Report on Patentability," for PCT Patent Application No. PCT/US2023/010469 mailed Jul. 25, 2024 (12 pages).
"Non-Final Office Action," for U.S. Appl. No. 18/215,603 mailed Jul. 18, 2024, 64 pages.
"Office Action," for Japanese Patent Application No. 2021-562795 mailed Jun. 18, 2024 (8 pages) with English translation.
"Response to Final Rejection," mailed Feb. 7, 2024, and the Advisory Action mailed on Jun. 4, 2024, for U.S. Appl. No. 16/167,140, submitted via EFS-Web on Jul. 2, 2024, 14 pages.
"Response to Non-Final Rejection," mailed on Apr. 25, 2024, for U.S. Appl. No. 16/167,079, submitted via EFS-Web on Jul. 25, 2024, 16 pages.
"Second Office Action," for Chinese Patent Application No. 202080030769.1 mailed Jul. 4, 2024 (13 pages) with English translation.
"Zenchi Examination Report," for Japanese Patent Application No. 2021-562966 mailed Aug. 6, 2024 (3 pages) with English Translation.
"Decision of Rejection," for Japanese Patent Application No. 2021-562966 mailed Dec. 26, 2023 (9 pages), with English translation.
"Fifth Office Action," for Chinese Patent Application No. 201880068897.8 mailed Feb. 8, 2024 (8 pages) with English summary.
"Final Office Action," for U.S. Appl. No. 16/167,140 mailed Feb. 7, 2024 (42 pages).
"First Office Action," for Chinese Patent Application No. 202080030771.9 mailed Nov. 15, 2023 (7 pages) with English summary.
"Non-Final Office Action," for U.S. Appl. No. 16/850,728 mailed Feb. 14, 2024 (33 pages).
"Non-Final Office Action," for U.S. Appl. No. 17/698,516 mailed Feb. 23, 2024 (69 pages).
"Response to Final Rejection," mailed on Sep. 14, 2023, for U.S. Appl. No. 16/167,079, submitted via EFS-Web on Dec. 14, 2023, 14 pages.
"Response to Non-Final Rejection," mailed on Nov. 14, 2024, for U.S. Appl. No. 16/166,957, submitted via EFS-Web on Feb. 14, 2024, 15 pages.
"Response to Non-Final Rejection," mailed on Oct. 11, 2024, for U.S. Appl. No. 16/167,140, submitted via EFS-Web on Jan. 11, 2024, 12 pages.
"Response to Non-Final Rejection," mailed on Sep. 19, 2023, for U.S. Appl. No. 16/167,087, submitted via EFS-Web on Dec. 19, 2023, 13 pages.
"Second Office Action," for Chinese Patent Application No. 201880078118.2 mailed Jan. 12, 2024 (17 pages) with English translation.
"Written Submissions," as filed in response to Summons to Attend Oral Proceedings for European Patent Application No. 18801134.0 filed Dec. 20, 2023 (137 pages).
"Communication Pursuant to Article 94(3) EPC," for European Patent Application No. 20724703.2 mailed Jun. 4, 2024 (7 pages).
"Extended European Search Report," for European Patent Application No. 24159633.7 mailed Jun. 14, 2024 (7 pages).
"Extended European Search Report," for European Patent Application No. 24171838.6 mailed May 8, 2024 (6 pages).
"Final Office Action," for U.S. Appl. No. 16/166,957 mailed May 31, 2024 (49 pages).
"Final Office Action," for U.S. Appl. No. 16/167,087 mailed Apr. 1, 2024 (38 pages).
"Final Rejection Action," for Chinese Patent Application No. 201880078118.2 mailed Mar. 28, 2024 (10 pages) with English translation, 12 pages.
"First Office Action," for Chinese Patent Application No. 202080030415.7 mailed Mar. 6, 2024 (13 pages) with English translation.
"First Office Action," for Chinese Patent Application No. 202080030769.1 mailed Dec. 29, 2023, with English summary (12 pages).

(56) References Cited

OTHER PUBLICATIONS

"First Office Action," for Chinese Patent Application No. 202080030850.X mailed Mar. 29, 2024 (14 pages) with English translation.
"First Office Action," for Chinese Patent Application No. 202080030856.7 mailed Mar. 16, 2024 (11 pages) with English translation.
"Non-Final Office Action," for U.S. Appl. No. 16/167,079 mailed Apr. 25, 2024 (34 pages).
"Non-Final Office Action," for U.S. Appl. No. 18/227,021 mailed May 31, 2024 (61 pages).
"Notice of Allowance," for U.S. Appl. No. 16/850,728 mailed Jun. 5, 2024 (17 pages).
"Response to Final Rejection," mailed on Feb. 7, 2024, for U.S. Appl. No. 16/167,140, submitted via EFS-Web on May 7, 2024, 12 pages.
"Response to Non-Final Rejection," mailed on Feb. 14, 2024, for U.S. Appl. No. 16/850,728, submitted via EFS-Web on May 14, 2024, 12 pages.
"Response to Non-Final Rejection," mailed on Feb. 23, 2024, for U.S. Appl. No. 17/698,516, submitted via EFS-Web on May 20, 2024, 9 pages.
"Second Office Action," for Chinese Patent Application No. 201880068852.0 mailed Jan. 15, 2024 (19 pages) with English summary.
Chen, Yu, et al. "Synergistic chemo-photodynamic therapy mediated by light-activated ROS-degradable nanocarriers.," Synergistic chemo-photodynamic therapy mediated by light-activated ROS-degradable nanocarriers. J. Mater. Chem. B, 2019, 7, 460-468. Apr. 12, 2018 (Chen et al.) https://pubs.rsc.org/en/content/articlelanding/20_I_9/tb/c8tb03030h, 460-468.

\* cited by examiner

ELECTRICAL STIMULATION FOR CANCER TREATMENT WITH INTERNAL AND EXTERNAL ELECTRODES

This application is a continuation application of U.S. Pat. No. 11,607,542, issued Mar. 21, 2023, which claims the benefit of U.S. Provisional Application No. 62/837,401, filed Apr. 23, 2019, the contents of which are herein incorporated by reference in their entirety.

FIELD

Embodiments herein relate to medical devices and methods for using the same to treat cancerous tumors within a bodily tissue. More specifically, embodiments herein relate to using medical devices configured to generate therapeutic electric fields at the site of a cancerous tumor.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

SUMMARY

In a first aspect, a medical device system is included having at least one electric field generating circuit configured to generate one or more electric fields; and control circuitry in communication with the electric field generating circuit, the control circuitry configured to control delivery of the one or more electric fields from the at least one electric field generating circuit; and two or more electrodes to deliver the electric fields to the site of a cancerous tumor within a patient; wherein at least one electrode is configured to be implanted; wherein at least one electrode is configured to be external; wherein the control circuitry causes the electric field generating circuit to generate one or more electric fields at frequencies selected from a range of between 10 kHz to 1 MHz.

In a second aspect, in addition to one or more of the preceding or following aspects, or in the alternative to some aspects, further can include a first lead providing electrical communication between the control circuitry and the at least one electrode configured to be implanted; and a second lead providing electrical communication between the control circuitry and the at least one electrode configured to be external.

In a third aspect, in addition to one or more of the preceding or following aspects, or in the alternative to some aspects, the first lead can include a percutaneous lead.

In a fourth aspect, in addition to one or more of the preceding or following aspects, or in the alternative to some aspects, wherein at least two electrodes are configured to be implanted and at least two electrodes are configured to be external.

In a fifth aspect, in addition to one or more of the preceding or following aspects, or in the alternative to some aspects, wherein the electric fields are delivered across at least one vector including both an implanted electrode and an external electrode.

In a sixth aspect, in addition to one or more of the preceding or following aspects, or in the alternative to some aspects, wherein the electric fields are delivered across at least two vectors, wherein a first vector is defined by a first pair of electrodes, wherein both electrodes of the first pair are implanted; wherein a second vector is defined by a second pair of electrodes; wherein both electrodes of the second pair are external.

In a seventh aspect, in addition to one or more of the preceding or following aspects, or in the alternative to some aspects, wherein the electric fields along the at least two vectors are substantially orthogonal to one another.

In an eighth aspect, in addition to one or more of the preceding or following aspects, or in the alternative to some aspects, can include at least two electric field generating circuits, wherein a first electric field generating circuit is implanted and a second electric field generating circuit is external.

In a ninth aspect, in addition to one or more of the preceding or following aspects, or in the alternative to some aspects, can include at least one implanted housing, the implanted housing defining an interior volume into which a first electric field generating circuit and a first control circuit are disposed; and at least one external housing, the external housing defining an interior volume into which a second electric field generating circuit and a second control circuit are disposed.

In a tenth aspect, in addition to one or more of the preceding or following aspects, or in the alternative to some aspects, wherein the electric field strength is greater at the site of the electrode that is configured to be non-implanted than at the site of the electrode that is configured to be implanted.

In an eleventh aspect, a method of treating a cancerous tumor is included, the method implanting one or more implanted electrodes inside a body of a patient with the cancerous tumor; placing one or more external electrodes on an outside surface of the body of the patient; generating an electrical field between at least one pair of electrodes, the electric field having frequencies within a range of between 10 kHz to 1 MHz.

In a twelfth aspect, in addition to one or more of the preceding or following aspects, or in the alternative to some aspects, further can include: ceasing generating the electrical field between the electrodes; moving the one or more electrodes on the outside surface of the body of the patient; and generating an electrical field between at least one pair of electrodes, the electric field having frequencies within a range of between 10 kHz to 1 MHz.

In a thirteenth aspect, in addition to one or more of the preceding or following aspects, or in the alternative to some aspects, wherein the at least one pair of electrodes includes at least one implanted electrode and at least one external electrode.

In a fourteenth aspect, in addition to one or more of the preceding or following aspects, or in the alternative to some aspects, can include generating electrical fields between respective electrodes of at least two electrode pairs; wherein a first electrode pair includes two implanted electrodes and a second electrode pair includes two external electrodes.

In a fifteenth aspect, in addition to one or more of the preceding or following aspects, or in the alternative to some aspects, wherein the implanted electrodes are disposed on a fully implanted lead.

In a sixteenth aspect, a method of providing power to an implanted medical device is included, the method establishing a power transfer connection transcutaneously or percutaneously between an external power supply and the implanted medical device; supplying power from the external power supply to the implanted cancer treatment device through the power transfer connection; and storing the supplied power inside the implanted medical device; wherein the implanted medical device includes at least one electric field generating circuit configured to generate one or more electric fields; and control circuitry in communication with the electric field generating circuit, the control circuitry configured to control delivery of the one or more electric fields from the at least one electric field generating circuit; and an interface to electrically connect to two or more electrodes to deliver the electric fields to the site of a cancerous tumor within a patient.

In a seventeenth aspect, in addition to one or more of the preceding or following aspects, or in the alternative to some aspects, wherein establishing a power transfer connection percutaneously between the external power supply and the implanted medical device includes inserting a power supply probe connected to the external power supply percutaneously into a power connection receiver connected to the implanted medical device.

In an eighteenth aspect, in addition to one or more of the preceding or following aspects, or in the alternative to some aspects, wherein establishing a power transfer connection transcutaneously between the external power supply and the implanted medical device includes establishing a transcutaneous inductive power transfer link.

In a nineteenth aspect, in addition to one or more of the preceding or following aspects, or in the alternative to some aspects, wherein the power supplied from the external power supply is modulated to control electric field generation by the implanted medical device.

In a twentieth aspect, in addition to one or more of the preceding or following aspects, or in the alternative to some aspects, wherein the implanted medical device is configured to send a wireless signal for receipt by a secondary device outside of the body, the signal can include information regarding charge level of a battery associated with the implanted cancer treatment device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
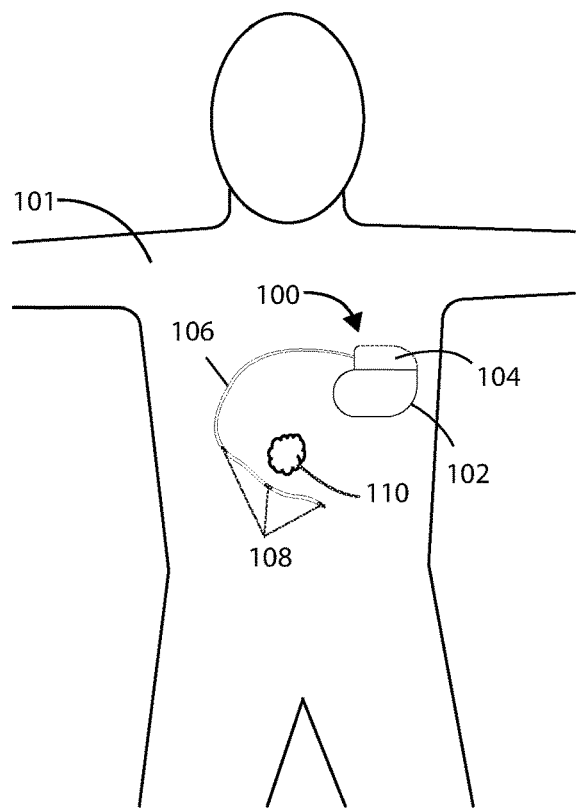
FIG. 1 is a schematic view of a medical system in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few.

While not intending to be bound by theory, it is believed that electric fields can disrupt mitosis within a cancerous tumor, such as by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances an electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules, can result in apoptosis (i.e., programmed cell death). It is also believed that alternating electric fields can lead to increased electric field density near the cleavage furrow of the dividing cells during telophase. An increased electric field density in the region of the cleavage furrow can result in dielectrophoresis of charged macromolecules, such as proteins and nucleic acids, toward the high electric field density at the furrow. The unequal concentration of key macromolecules required for cellular division at the site of the cleavage furrow can disrupt the final separation of the sister cells during telophase and eventually lead to apoptosis.

Various embodiments disclosed herein include a medical device system that can generate an electric field for treatment of cancer that can include, or can control, at least one implanted electrode and at least one electrode that is external to the patient's body. Internal electrodes can be advantageous as they can be positioned close to a treatment area (such as a cancerous tumor) and deliver and/or sense an electric field without substantial intervening tissue that diminished field strength. External electrodes can be advantageous because they can be moved more easily than most internal electrodes allowing for changes to the positions of electrodes used to deliver and/or sense electric fields. Such movement of electrodes can be desirable to account for changes to a tumor that is being treated and to accommodate desired changes in the stimulation and/or sense vectors. By including both implanted and external electrodes, desirable aspects of each approach can be combined to deliver electrical stimulation with high field strength to the desired treatment site while allowing for electrodes to be moved to change vectors as desired.

Referring now to FIG. 1, a schematic view is shown of a medical device 100 in accordance with various embodiments herein. The medical device 100 can be implanted entirely within the body of a patient 101 at or near the site of a cancerous tumor 110 located within a bodily tissue. Various implant sites can be used including areas such as in the limbs, the upper torso, the abdominal area, the head, and the like.

Figure 2:
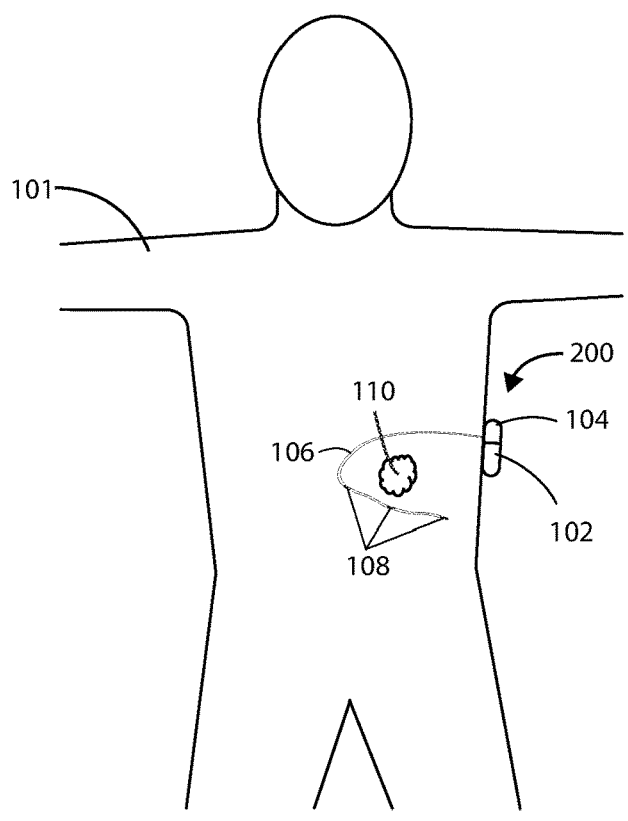
FIG. 2 is a schematic view of a medical system in accordance with various embodiments herein.

Referring now to FIG. 2, another schematic view is shown of a medical device 200 in accordance with various embodiments herein. The medical device 200 can be external but can be connected to an element, such as leads, that are at least partially implanted within the body of a patient 101. In some embodiments, the medical device 200 can be partially implanted and partially external to the body of a patient. In some embodiments, the medical device 200 can include a transcutaneous or percutaneous connection between components disposed internal to the body and external to the body. In various embodiments, the medical device system described herein can include an implanted medical device 100 and an external medical device 200. In other embodiments, the medical device system described herein can include a partially implanted medical device.

An implanted portion of a medical device system, such as an implanted medical device 100 or portion thereof, can wirelessly communicate patient identification data, diagnostic information, electric field data, physiological parameters, software updates, and the like with a fully or partially external portion of a medical device 200 over a wireless connection. Implanted medical device 100 can also wirelessly communicate with an external device configured to wirelessly charge the medical device utilizing inductance, radio frequency, and acoustic energy transfer techniques, and the like.

In some embodiments, a portion of a medical device or system can be entirely implanted and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include many of the same components as and can be configured to perform many of the same functions as a pulse generator. In embodiments where a portion of a medical device is entirely implanted and a portion of the medical device is entirely external, the portion of the medical device that is entirely external can communicate wirelessly with the portion of the medical device that is entirely internal. However, in other embodiments a wired connection can be used for the implanted portion to communication with the external portion.

The implanted medical device 100 and/or the medical device 200 can include a housing 102 and a header 104 coupled to the housing 102. Various materials can be used to form the housing 102. In some embodiments, the housing 102 can be formed of a material such as a metal, ceramic, polymer, composite, or the like. In some embodiments, the housing 102, or one or more portions thereof, can be formed of titanium. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow.

In some embodiments where a portion of the medical device 100 or 200 is partially external, the header 104 and housing 102 can be surrounded by a protective casing made of durable polymeric material. In other embodiments, where a portion of a device is partially external, the header 104 and housing 102 can be surrounded by a protective casing made of one or more of a polymeric material, metallic material, and/or glass material.

The header 104 can be coupled to one or more leads 106. The header 104 can serve to provide fixation of the proximal end of one or more leads 106 and electrically couple the one or more leads 106 to one or more components within the housing 102. The one or more leads 106 can include one or more electrodes 108 disposed along the length of the electrical leads 106. In some embodiments, electrodes 108 can include electric field generating electrodes and in other embodiments electrodes 108 can include electric field sensing electrodes. In some embodiments, leads 106 can include both electric field generating and electric field sensing electrodes. In other embodiments, leads 106 can include any number of electrodes that are both electric field sensing and electric field generating. The leads 106 can include one or more conductors therein, such as metal wires, to provide electrical communication between the electrodes and a proximal end (or plug) of the lead. The wires can exist as single strands or fibers or can be multifibrillar such as a cable. The leads 106 can include a shaft, typically formed of a polymeric material or another non-conductive material, within which the conductors therein can pass. The proximal end of the leads 106 can be inserted into the header 104, thereby providing electrical communication between the electrodes 108 and the components inside the housing 102. It will be appreciated that while many embodiments of medical devices herein are designed to function with leads, leadless medical devices that generate electrical fields are also contemplated herein.

In various embodiments, the electrodes 108 can be positioned around or adjacent to a tumor 110, such as a cancerous tumor. The tumor 110 can be positioned within an electric field generated by the electrodes 108.

The electric fields generated by the implanted medical device 100 and/or the medical device 200 can vary. In some embodiments, the implanted medical device 100 and/or the medical device 200 can generate one or more electric fields at frequencies selected from a range of between 10 kHz to 1 MHz.

Figure 3:
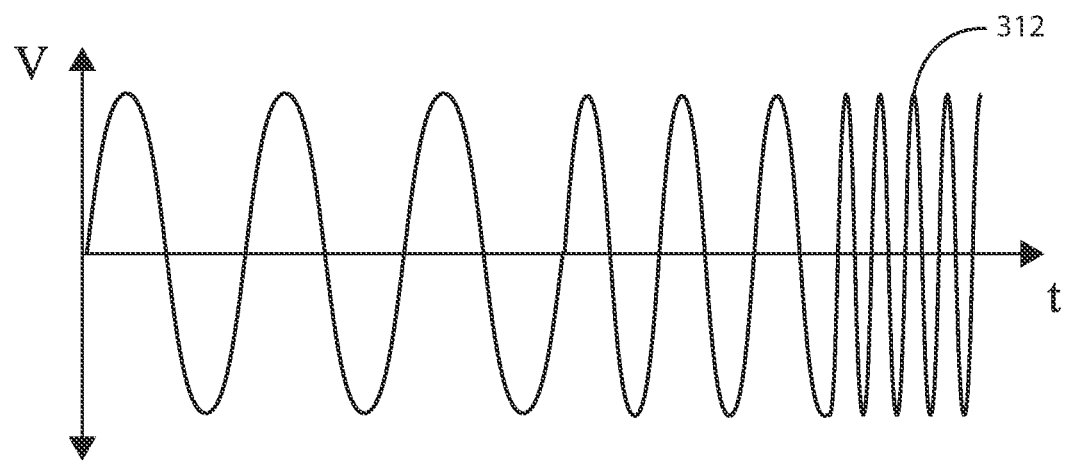
FIG. 3 is a plot of an exemplary therapy parameter in accordance with various embodiments herein.
Figure 4:
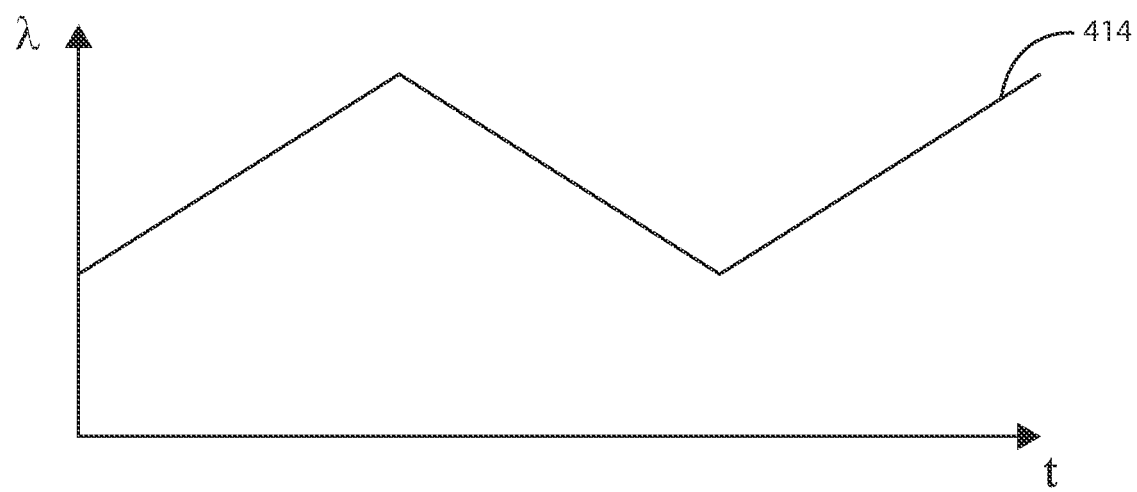
FIG. 4 is a plot of an exemplary therapy parameter in accordance with various embodiments herein.

In some embodiments, an electric field can be applied to the site of a cancerous tumor at a specific frequency or constant frequency range. However, in some embodiments, an electric field can be applied to the site of a cancerous tumor by sweeping through a range of frequencies. As one example, referring now to FIG. 3, exemplary plot 312 shows an alternating electric field, delivered by the electrodes 108, where the frequency increases over time. Similarly, FIG. 4 shows the change in frequency as a function of time in exemplary plot 414 during a programmed therapy parameter. In some embodiments, a frequency sweep can include sweeping from a minimum frequency up to a maximum frequency. In some embodiments, a frequency sweep can include sweeping from a maximum frequency down to a minimum frequency. In other embodiments, sweeping from a minimum frequency up to a maximum frequency and sweeping from the maximum frequency down to the minimum frequency can be repeated as many times as desired throughout the duration of the delivery of the electric field from the electric field generating circuit.

As therapy progresses during a frequency sweep, it may be desired to alternate between frequency ranges so that as the cells within a population change in size and number in response to therapy, more cells can be targeted. For example, in some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy. In some embodiments, the second frequency sweep (range) can be at higher frequencies than the first frequency sweep (range). In some embodiments, the first frequency sweep (range) can be at higher frequencies than the second frequency sweep (range).

Frequency ranges for the first and second frequency ranges can be any range including specific frequencies recited above or below, provided that the lower end of each range is a value less than the upper end of each range. At times, it may be beneficial to have some amount of overlap between the frequency range of the first and second frequency sweep.

Medical Devices and Systems

Figure 5:
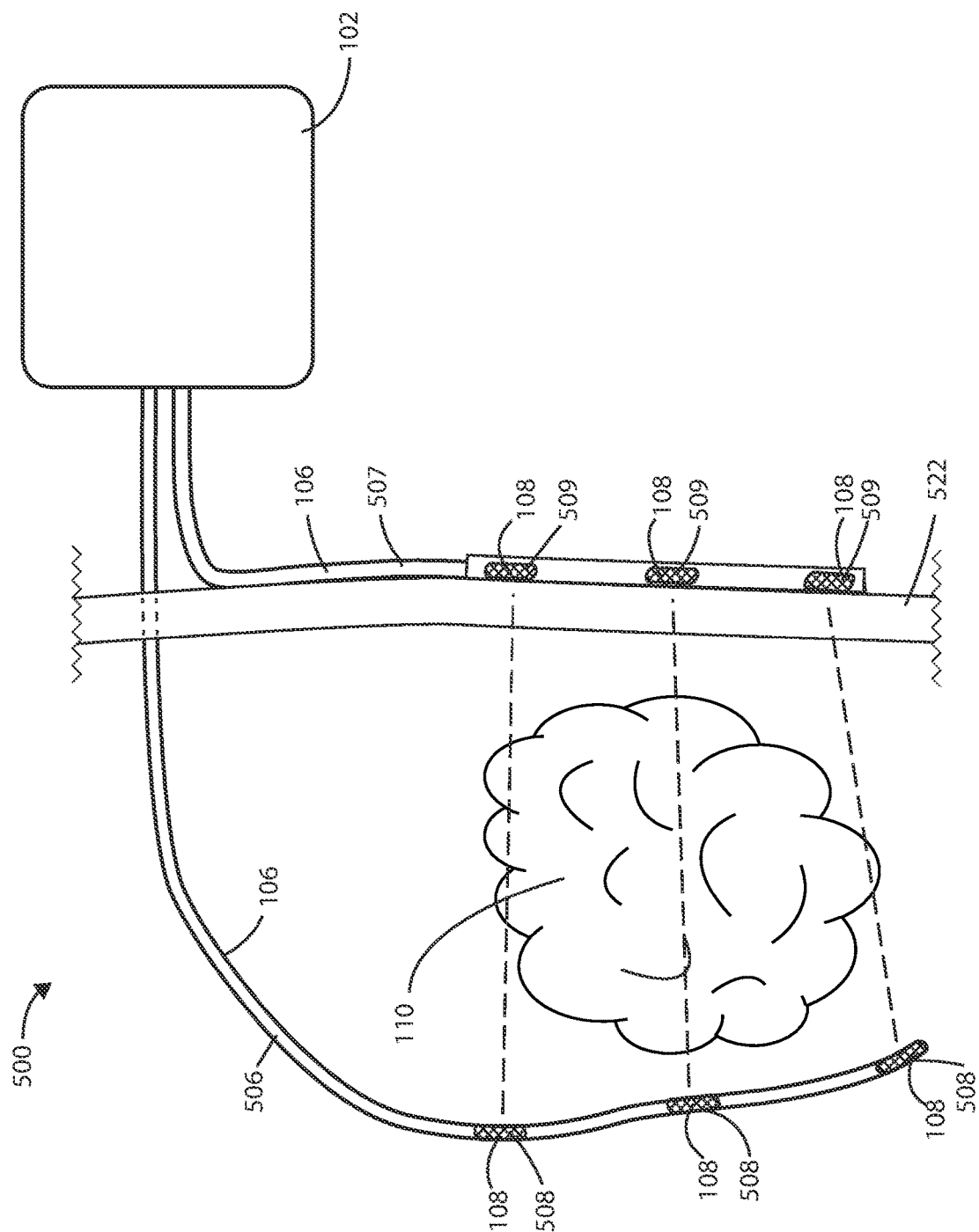
FIG. 5 is a schematic view of a medical device in accordance with various embodiments herein.

As described above, there can be various advantages associated with using combinations of implanted and external electrodes for delivery and/or sensing electrical fields. Referring now to FIG. 5, a schematic diagram of a medical device 500 is shown in accordance with the embodiments herein. The medical device 500 can include housing 102, one or more leads 106, at least one electric field generating circuit, and control circuitry. The electric field generating circuit can be disposed within the housing 102. The electric field generating circuit can be configured to generate one or more electric fields. The control circuitry can be in communication with the electric field generating circuit. The control circuitry can be configured to control delivery of the one or more electric fields from the electric field generating circuit. The control circuitry can cause the electric field generating circuit to generate one or more electric fields, such as at frequencies selected from a range between 10 kHz to 1 MHz, as further discussed below.

The leads 106 can include one or more electrodes such as electrodes 108 disposed along the length of the leads 106. In various embodiments, the electrodes 108 can deliver the electric fields to the site of a tumor, such as a cancerous tumor, within the patient. In some embodiments, the electrodes 108 can include electric field generating electrodes and, in other embodiments, the electrodes 108 can include electric field sensing electrodes. In some embodiments, the leads 106 can include both electric field generating and electric field sensing electrodes. In various embodiments, at least one electrode is configured to be implanted within the patient and at least one electrode is configured to be external to the patient. In various embodiments, one or more leads 106 can be implanted leads 506, and one or more leads 106 can be external leads 507. In various embodiments, one or more electrodes 108 can be implanted electrodes 508, and one or more electrodes 108 can be external electrodes 509. In some embodiments, at least two electrodes 508 are configured to be implanted and at least two electrodes 509 are configured to be external.

The proximal ends (or plugs) of leads 106 can be disposed within the header 104. The distal ends of electrical leads 106 can surround a tumor 110 such that the electrodes 108 are brought into proximity of the tumor 110. In some embodiments, the leads 106 can be positioned within the vasculature such that electrodes 108 are adjacent to or positioned within the tumor 110. However, it will be appreciated that leads 106 can be disposed in various places within or around the tumor 110. In some embodiments, the leads 106 can pass directly through the tumor 110.

In some embodiments, the leads 106 can include one or more tracking markers along the length of the lead for use in determining the precise location of the electrodes relative to the tumor. In some embodiments, the one or more tracking markers can be disposed directly distal or directly proximal to the one or more electrodes disposed on the lead. In some embodiments, the tracking markers can be formed from a magnetic material. In some embodiments, the tracking markers can be formed from a radiographic material. In some embodiments, the tracking markers can be formed from a fluorographic material.

It will be appreciated that a plurality of electric field vectors can be utilized between various combinations of electrodes 108 disposed along leads 106 to create an electric field. For example, one or more electric field vectors can be generated between the most proximal electrodes 108 on the two leads 106. Similarly, one or more electric field vectors can be generated between the distal most electrodes 108 on the two leads 106. It will also be appreciated that one or more electric field vectors can be generated between any combination of electrodes 108. In some embodiments, one or more electric field vectors can be generated between any combination of electrodes 108 and the housing 102 of the medical device 500. In some embodiments, the electric fields are delivered across at least one vector including both an implanted electrode and an external electrode. In various embodiments, the electric field strength can be greater at the site of the electrode 108 that is configured to be non-implanted (external) than at the site of the electrode 108 that is configured to be implanted, such as to account for the implanted electrode 108 being located closer to the tumor 110.

It will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

In various embodiments, a lead 106 can provide electrical communication between the control circuitry and the implanted electrode 108, and a second lead 106 can provide electrical communication between the control circuitry and the external electrode 108. In some embodiments, a lead 106 can be a percutaneous lead 106, such as a lead that extends through or across the skin 522 of the patient. The tissue designated by reference number 522 can include one or more of the epidermis, dermis, hypodermis, and/or other tissue beneath those layers. The implanted electrodes 108 can be disposed on a percutaneous lead 106.

In some embodiments, exposing the tumor 110 to an electric field can shrink or move the tumor 110, such that the original position of the electrodes 108 is no longer the most efficient or most desired. In such embodiments, the external electrodes 509 on the external lead 507 can be easily moved to account for the changes of the tumor 110.

Figure 6:
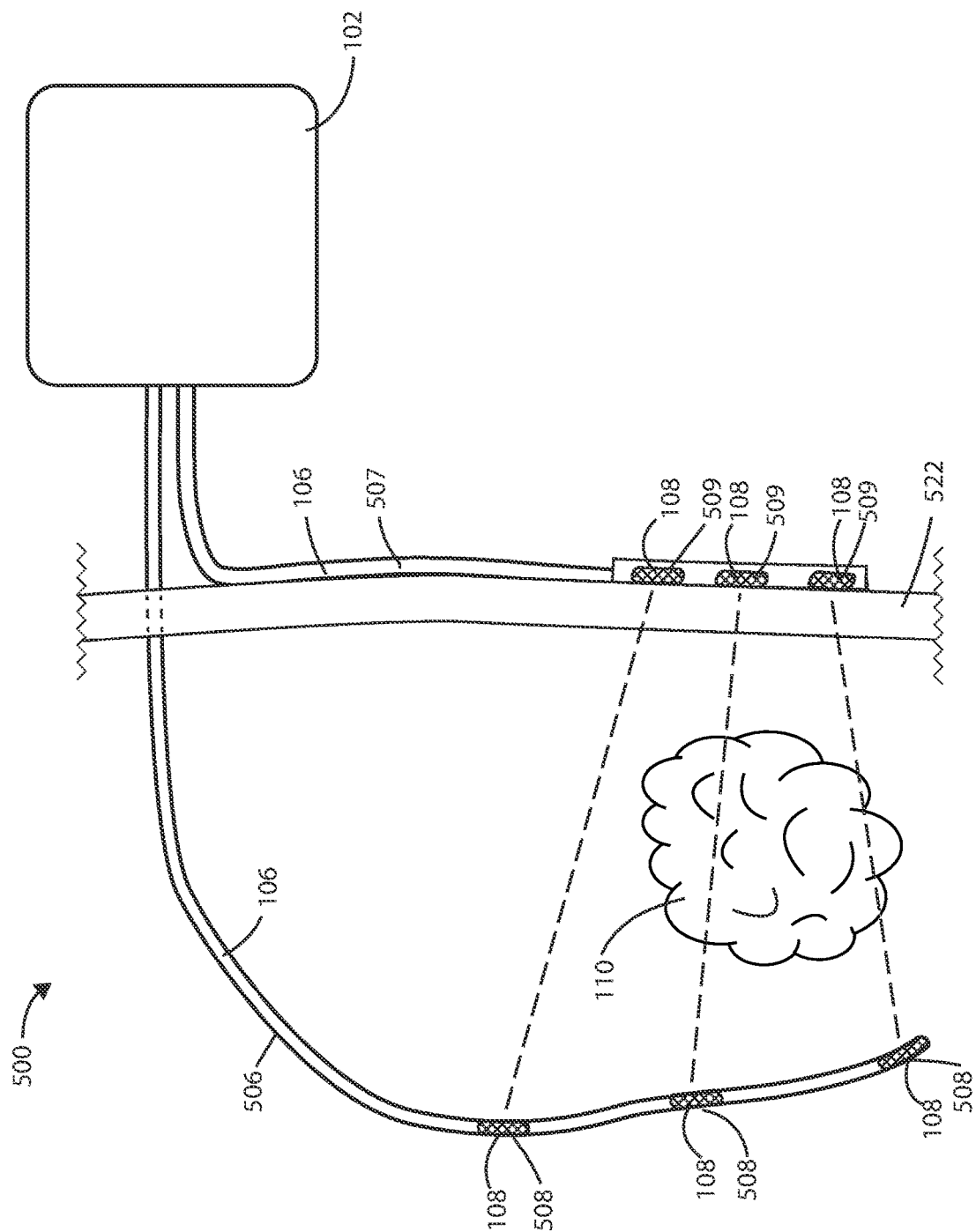
FIG. 6 is a schematic view of a medical device in accordance with various embodiments herein.

In comparing FIG. 5 to FIG. 6, it can be seen that the tumor 110 has shrunk, such as a result of treatment. As such, the external electrodes 509 on an outside surface of the body of the patient have been moved to a more efficient or desirable position.

In reference now to FIG. 6, it can be seen that the external electrodes 509 have been moved to affect the electrical field. In various embodiments, the electrical field between the electrodes 108 can be ceased, then one or more external electrodes 509 can be moved. After the external electrodes 509 have been repositioned, the electrical field can be generated once again to resume treatment. In many cases external electrodes 509 are easily moved or repositioned compared to implanted electrodes 508.

Figure 7:
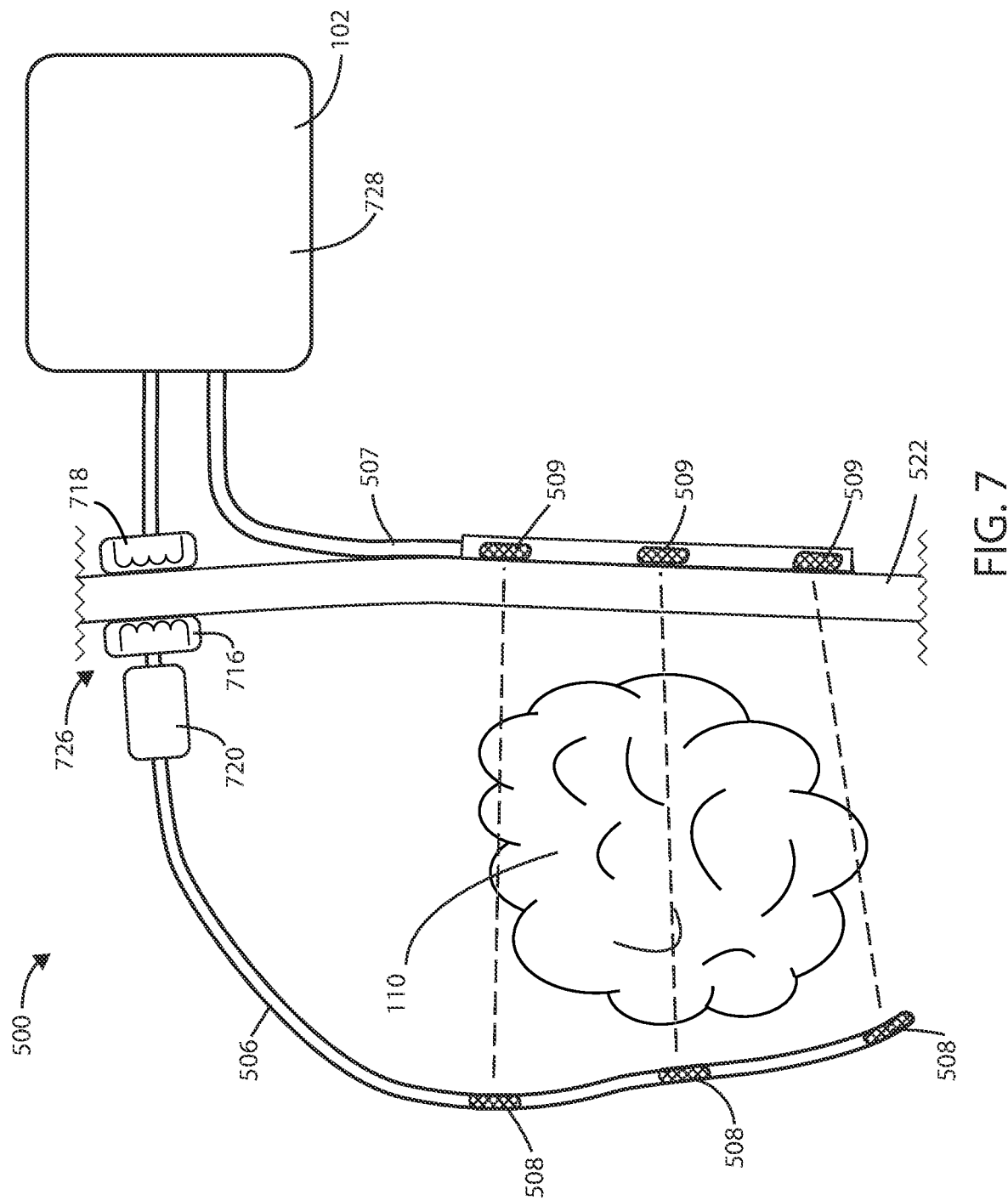
FIG. 7 is a schematic view of a medical device in accordance with various embodiments herein.

In reference now to FIG. 7, a schematic view of a medical device 500 is shown in accordance with various embodiments herein. In some embodiments, the implanted lead 506 can terminate within the patient, such that the lead 106 does not extend through or across the patient's skin 522.

In some embodiments, a wireless power transfer connection 726 can be established transcutaneously between an external power supply 728, such as a power supply within the housing 102, and an implanted lead 506. In some embodiments, the medical device 500 can include an inductive power transfer link, including paired internal 716 and external 718 inductors to transfer power from outside of the body to an implanted component of the system. The inductive power transfer link can allow for a transfer of power from an external power supply 728 to an internal control component 720, which in turn can cause an electrical field to be generated with the implanted electrodes 508 without puncturing the skin 522 or otherwise requiring a maintained opening or tunnel through the patient's skin 522. In some embodiments, the internal control component can include a battery or one or more capacitors to store enough energy to maintain delivering an electrical field for at least a period of time. In some embodiments, the internal control component includes one or more capacitors, but not a battery. In some embodiments, the internal control component 720 can include circuitry and components therein similar or the same as that described with respect to FIGS. 13 and 14 herein. In some embodiments, the transferred power provided from the external power supply 728 can be modulated to control the electrical field as provided through the implanted electrodes 508. For example, the transferred power can be used as a control signal to control aspects of electrical field generation including, but not limited to, frequency, duty cycle, electrical field strength, and the like.

Figure 8:
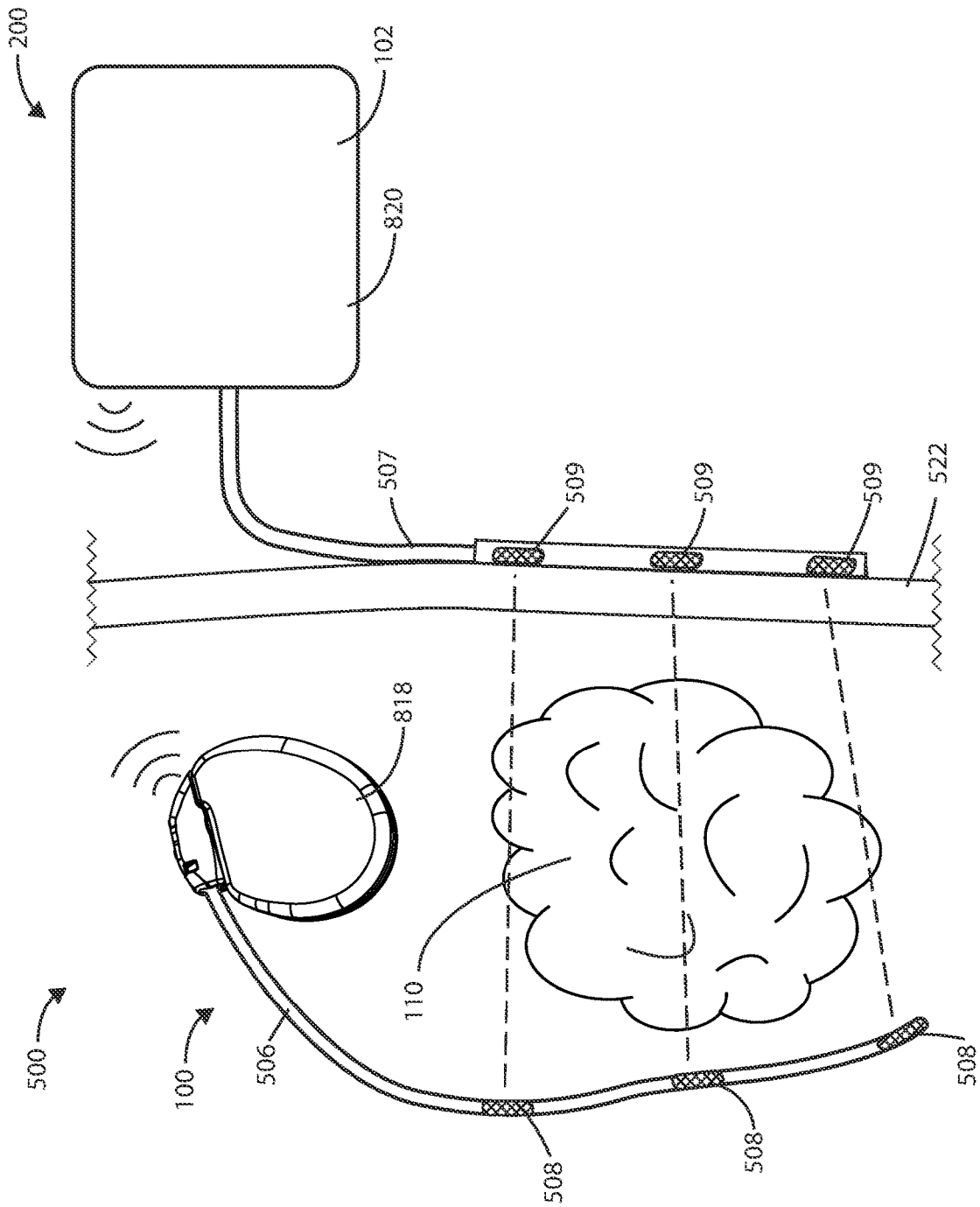
FIG. 8 is a schematic view of a medical device in accordance with various embodiments herein.

Referring now to FIG. 8, a schematic view of a medical device 500 is shown in accordance with various embodiments herein. The medical device 500 can include an implanted medical device 100 and an external medical device 200. In some embodiments, the medical device 500 can include at least one implanted housing 818. The implanted housing 818 can define an interior volume. An electric field generating circuit and a control circuit can be disposed within the interior volume of the housing 818. In some embodiments, the implanted electrodes 508 can be disposed on a fully implanted lead 506, such as a lead 506 with both the proximal end and the distal end terminating within the patient's body.

The medical device 500 can further include at least one external housing 820. The external housing 820 can define an interior volume. A second electric field generating circuit and control circuit can be disposed within the interior volume of the housing 820.

In various embodiments, an implanted medical device 100, such as the implanted housing 818, can be configured to send a wireless signal for receipt by an external medical device 200, such as the external housing 820. Similarly, an external medical device 200, such as the external housing 820, can be configured to send a wireless signal for receipt by an implanted medical device 100, such as the implanted housing 818. In various embodiments, the wireless signal can include various information, such as information regarding charge level of a battery associated with the implanted cancer treatment device. Other information can also be transferred between the implanted device and the external device wirelessly, such as treatment parameters and sensor readings.

Figure 9:
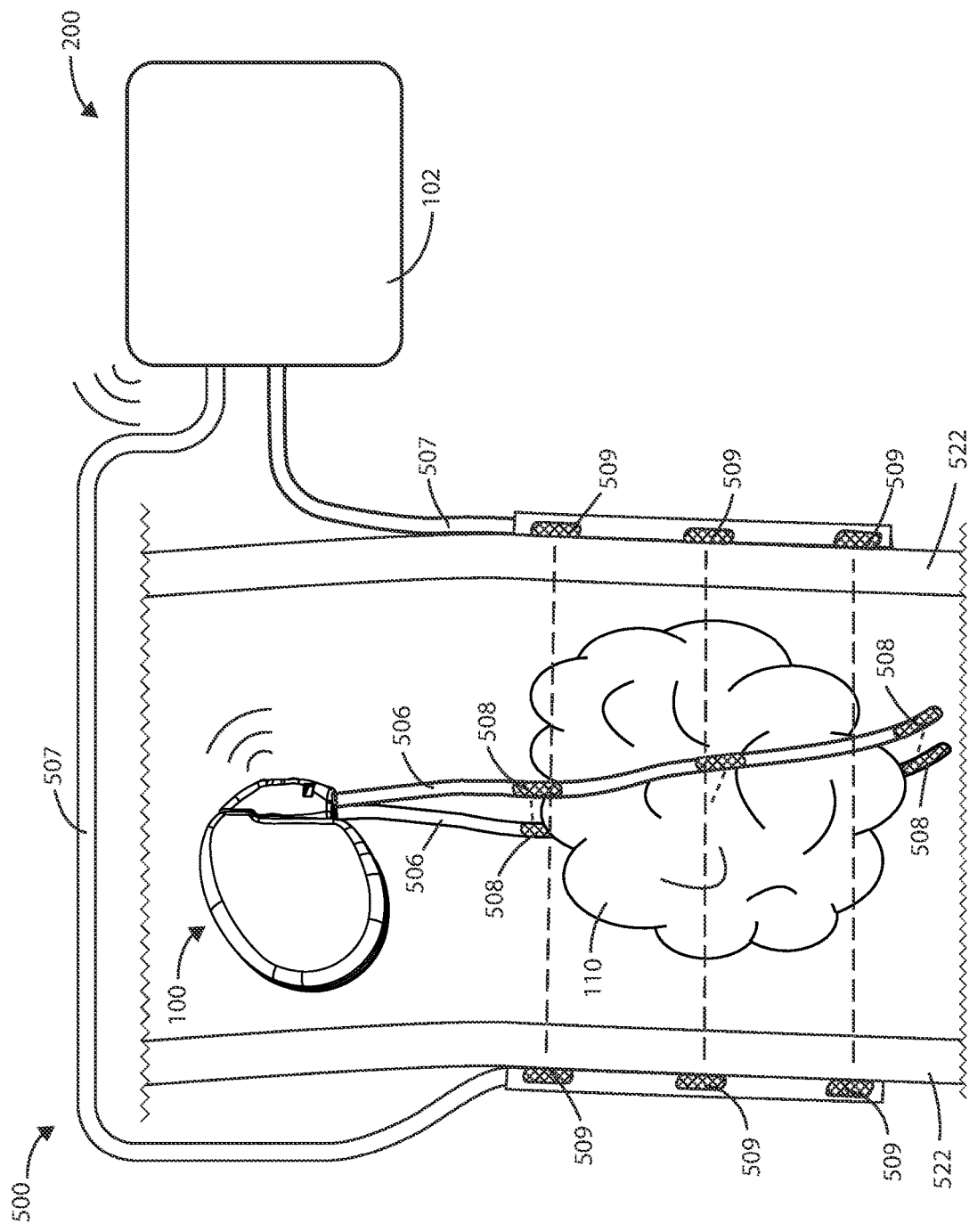
FIG. 9 is a schematic view of a medical device in accordance with various embodiments herein.

FIG. 9 shows a schematic view of a medical device 500 in accordance with various embodiments herein. The medical device 500 can include an implanted medical device 100 and an external medical device 200. In some embodiments, the medical device 500 can include two electric field generating circuits. The implanted medical device 100 can include a first electric field generating circuit and the external medical device 200 can include a second electric field generating circuit. In various embodiment, the implanted medical device 100 can be entirely located within the patient, and the external medical device 200 can be entirely located outside of the patient's body, such that no physical components extend through or across the patient's skin 522.

In some embodiments, the implanted medical device 100 can include two or more leads 506, and the external medical device 200 can include two or more leads 507. The leads 506 can include electrodes 508. The leads 507 can include electrodes 509. In some embodiments, the electric fields can be delivered across at least two vectors, such as first vector defined by a pair of electrodes 508 that are both implanted, and a second vector defined by a pair of electrodes 509 that are both external. In some embodiments, such as shown in FIG. 9, the electric fields along the two vectors can be substantially orthogonal to one another.

External Power Supply

In some embodiments, a power transfer connection 1026 can be established transcutaneously or percutaneously between an external power supply 1028 and an implanted medical device 100. In reference now to FIG. 10, a schematic view of a medical device 500 is shown in accordance with various embodiments herein. In some embodiments, the medical device 500 can include an implanted medical device 100 and an external power supply 1028. The power can be supplied from the external power supply 1028 to the implanted medical device 100 through a power supply probe 1032, such as a needle. The external power supply 1028 can include the power supply probe 1032. The implanted medical device 100 can include a power connection receiver 1034.

In some embodiments, the power connection receiver 1034 can be configured to receive a portion of the power supply probe 1032, such as to transfer power or communication signals between the implanted device 100 and the external power supply 1028. Power can be supplied by the external power supply 1028 and stored inside the implanted medical device 100.

In various embodiments, establishing a power transfer connection 1026 percutaneously between the external power supply 1028 and the implanted device 100 can include inserting the power supply probe 1032 connected to the external power supply 1028 percutaneously into the power connection receiver 1034 connected to the implanted medical device 100. In various embodiments, power supplied from the external power supply 1028 can be modulated to control electric field generation by the implanted medical device 100.

Power supplied to the implanted medical device 100 can be stored in the implanted medical device 100, such as for usage at a future time. The power can be stored within the implanted medical device 100 such that the power transfer connection 1026 does not need to be maintained for the implanted medical device 100 to operate. The power transfer connection 1026 can be established when needed, such as to recharge a battery in the implanted medical device 100.

In some embodiments, the power supply probe 1032 can extend through the patient's skin 522 to insert into the power connection receiver 1034. In various embodiments, when the power supply probe 1032 is not connected to the power connection receiver 1034, the patient's skin 522 can heal and cover the power connection receiver 1034. In some embodiments, to reestablish the power transfer connection 1026, the power supply probe 1032 can puncture or penetrate through the patient's skin 522 and connect with the power connection receiver 1034.

Figure 11:
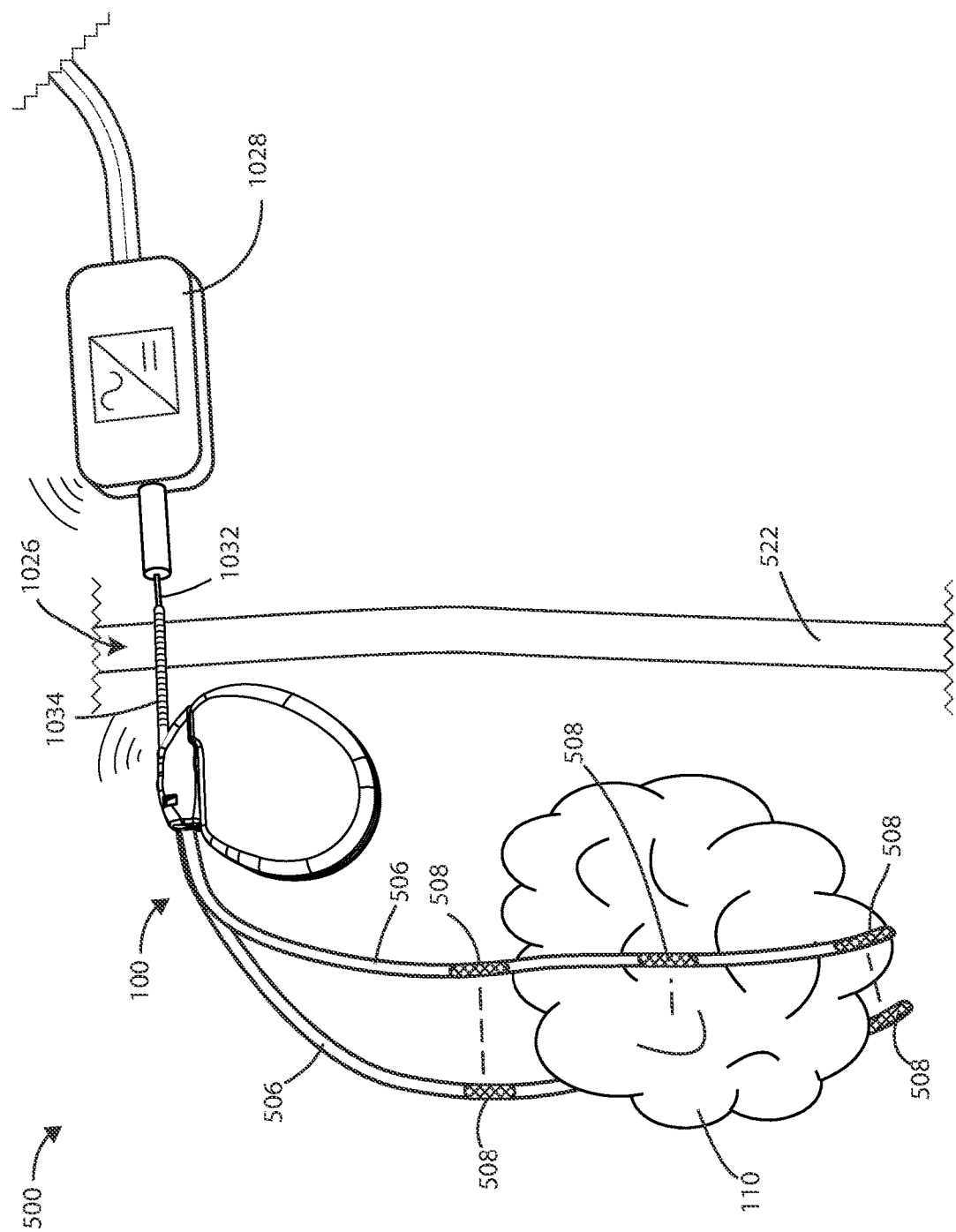
FIG. 11 is a schematic view of a medical device in accordance with various embodiments herein.

In reference now to FIG. 11, a schematic of a medical device 500 is shown in accordance with various embodiments. In some embodiments, the power connection receiver 1034 can extend through the skin 522, such that the power supply probe 1032 can connected with the power connection receiver 1034 without extending through the patient's skin 522 or without creating a new aperture in the patient's skin 522. In various embodiments, the external power supply 1028 can be in wireless communication with the implanted medical device 100, such as to relay information regarding battery charge status or treatment parameters.

Figure 12:
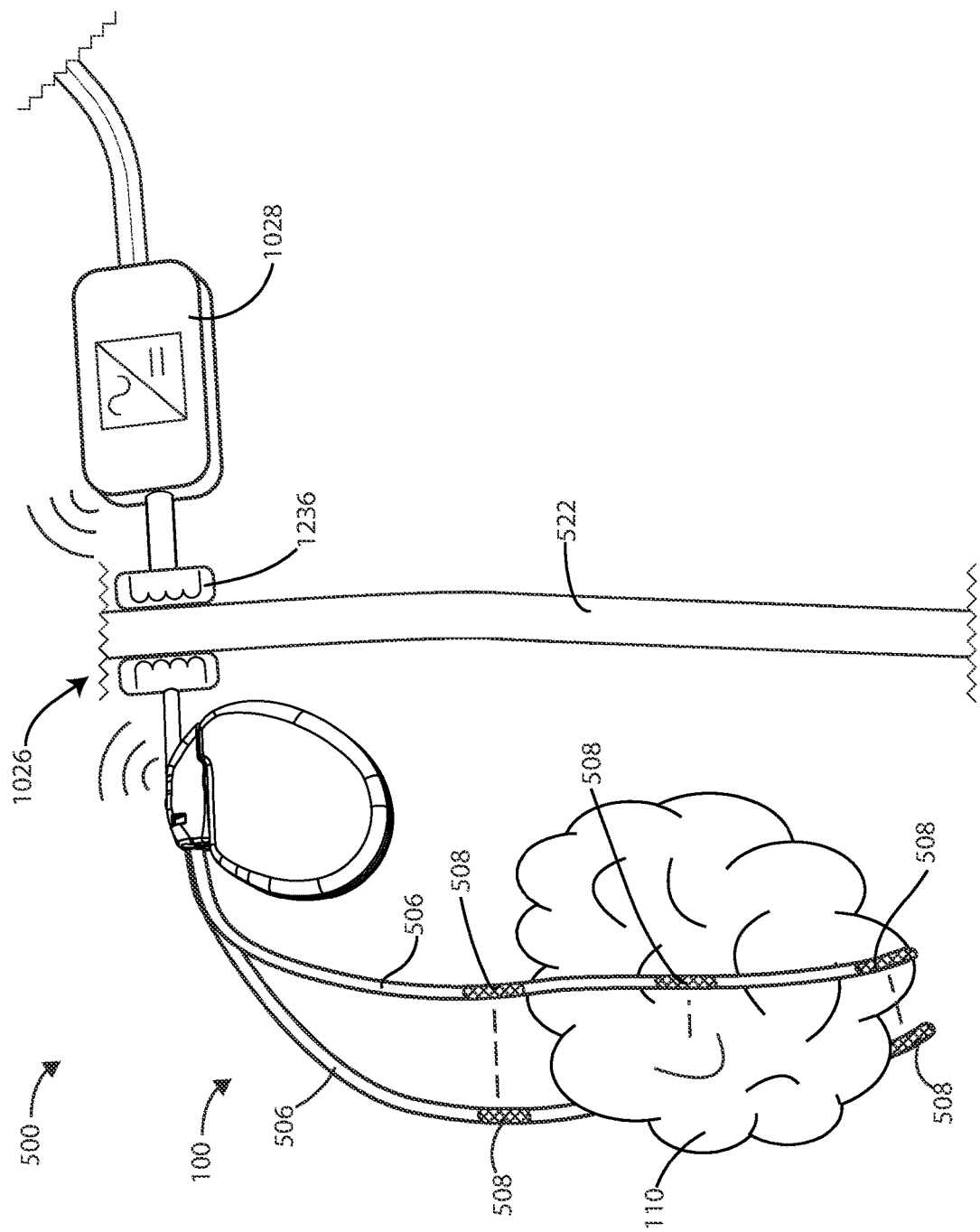
FIG. 12 is a schematic view of a medical device in accordance with various embodiments herein.

In reference now to FIG. 12, a schematic of a medical device 500 is shown in accordance with various embodiments. The medical device 500 can include an external power supply 1028 and an implanted medical device 100. In some embodiments, the power transfer connection 1026 can include a transcutaneous inductive power transfer link 1236. In some embodiments, the power supplied from the external power supply 1028 can be modulated to control electric field generation by the implanted device 100.

Figure 13:
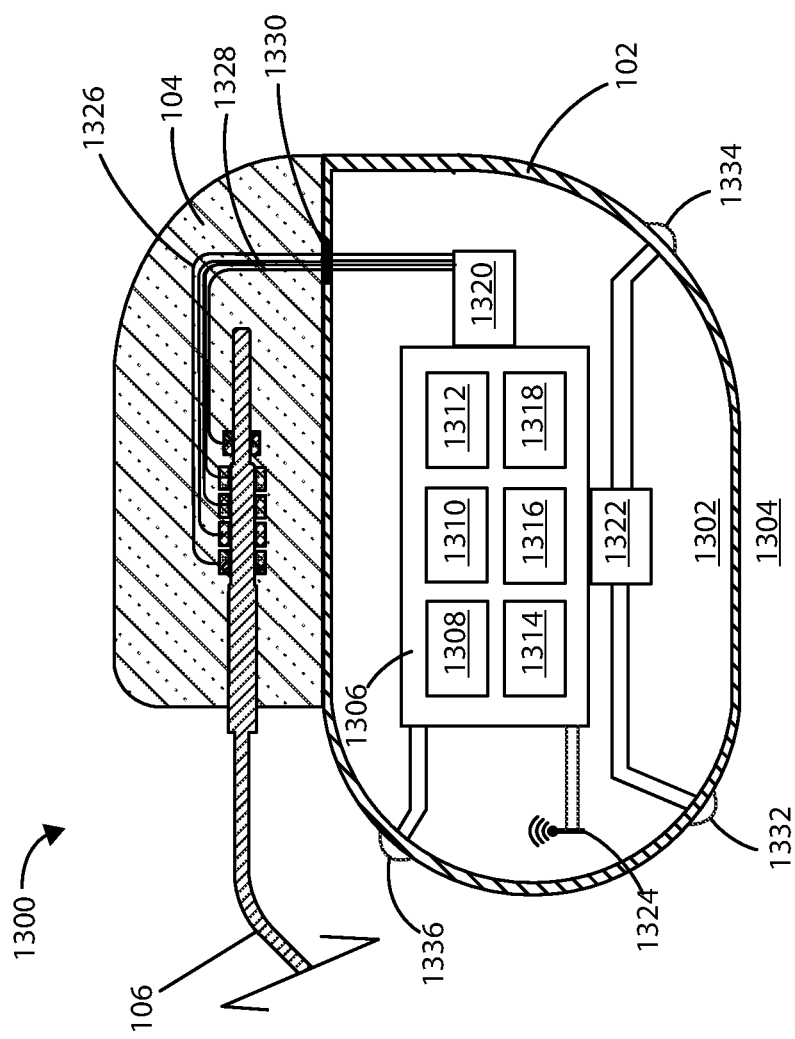
FIG. 13 is a schematic cross-sectional view of a medical device in accordance with various embodiments herein.

Referring now to FIG. 13, a schematic cross-sectional view of medical device 1300 is shown in accordance with various embodiments herein. The housing 102 can define an interior volume 1302 that can be hollow and that in some embodiments is hermetically sealed off from the area 1304 outside of medical device 1300. In other embodiments the housing 102 can be filled with components and/or structural materials such that it is non-hollow. The medical device 1300 can include control circuitry 1306, which can include various components 1308, 1310, 1312, 1314, 1316, and 1318 disposed within housing 102. In some embodiments, these components can be integrated and in other embodiments these components can be separate. In yet other embodiments, there can be a combination of both integrated and separate components. The medical device 1300 can also include an antenna 1324, to allow for unidirectional or bidirectional wireless data communication, such as with an external device or an external power supply. In some embodiments, the components of medical device 1300 can include an inductive energy receiver coil (not shown) communicatively coupled or attached thereto to facilitate transcutaneous recharging of the medical device via recharging circuitry.

The various components 1308, 1310, 1312, 1314, 1316, and 1318 of control circuitry 1306 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 1306 can be in communication with an electric field generating circuit 1320 that can be configured to generate electric current to create one or more fields. The electric field generating circuit 1320 can be integrated with the control circuitry 1306 or can be a separate component from control circuitry 1306. Control circuitry 1306 can be configured to control delivery of electric current from the electric field generating circuit 1320. In some embodiments, the electric field generating circuit 1320 can be present in a portion of the medical device that is external to the body.

In some embodiments, the control circuitry 1306 can be configured to direct the electric field generating circuit 1320 to deliver an electric field via leads 106 to the site of a cancerous tumor located within a bodily tissue. In other embodiments, the control circuitry 1306 can be configured to direct the electric field generating circuit 1320 to deliver an electric field via the housing 102 of medical device 1300 to the site of a cancerous tumor located within a bodily tissue. In other embodiments, the control circuitry 1306 can be configured to direct the electric field generating circuit 1320 to deliver an electric field between leads 106 and the housing 102 of medical device 1300. In some embodiments, one or more leads 106 can be in electrical communication with the electric field generating circuit 1320.

In some embodiments, various components within medical device 1300 can include an electric field sensing circuit 1322 configured to generate a signal corresponding to sensed electric fields. Electric field sensing circuit 1322 can be integrated with control circuitry 1306 or it can be separate from control circuitry 1306.

Sensing electrodes can be disposed on or adjacent to the housing of the medical device, on one or more leads connected to the housing, on a separate device implanted near or in the tumor, or any combination of these locations. In some embodiments, the electric field sensing circuit 1322 can include a first sensing electrode 1332 and a second sensing electrode 1334. In other embodiments, the housing 102 itself can serve as a sensing electrode for the electric field sensing circuit 1322. The electrodes 1332 and 1334 can be in communication with the electric field sensing circuit 1322. The electric field sensing circuit 1322 can measure the electrical potential difference (voltage) between the first electrode 1332 and the second electrode 1334. In some embodiments, the electric field sensing circuit 1322 can measure the electrical potential difference (voltage) between the first electrode 1332 or second electrode 1334, and an electrode disposed along the length of one or more leads 106. In some embodiments, the electric field sensing circuit can be configured to measure sensed electric fields and to record electric field strength in V/cm.

It will be appreciated that the electric field sensing circuit 1322 can additionally measure an electrical potential difference between the first electrode 1332 or the second electrode 1334 and the housing 102 itself. In other embodiments, the medical device can include a third electrode 1336, which can be an electric field sensing electrode or an electric field generating electrode. In some embodiments, one or more sensing electrodes can be disposed along lead 106 and can serve as additional locations for sensing an electric field. Many combinations can be imagined for measuring electrical potential difference between electrodes disposed along the length of one or more leads 106 and the housing 102 in accordance with the embodiments herein.

In some embodiments, the one or more leads 106 can be in electrical communication with the electric field generating circuit 1320. The one or more leads 106 can include one or more electrodes 108, as shown in FIGS. 1 and 2. In some embodiments, various electrical conductors, such as electrical conductors 1326 and 1328, can pass from the header 104 through a feed-through structure 1330 and into the interior volume 1302 of medical device 1300. As such, the electrical conductors 1326 and 1328 can serve to provide electrical communication between the one or more leads 106 and control circuitry 1306 disposed within the interior volume 1302 of the housing 102.

In some embodiments, recorder circuitry can be configured to record the data produced by the electric field sensing circuit 1322 and record time stamps regarding the same. In some embodiments, the control circuitry 1306 can be hardwired to execute various functions, while in other embodiments the control circuitry 1306 can be directed to implement instructions executing on a microprocessor or other external computation device. A telemetry circuit can also be provided for communicating with external computation devices such as a programmer, a home-based unit, and/or a mobile unit (e.g., a cellular phone, personal computer, smart phone, tablet computer, and the like).

Figure 14:
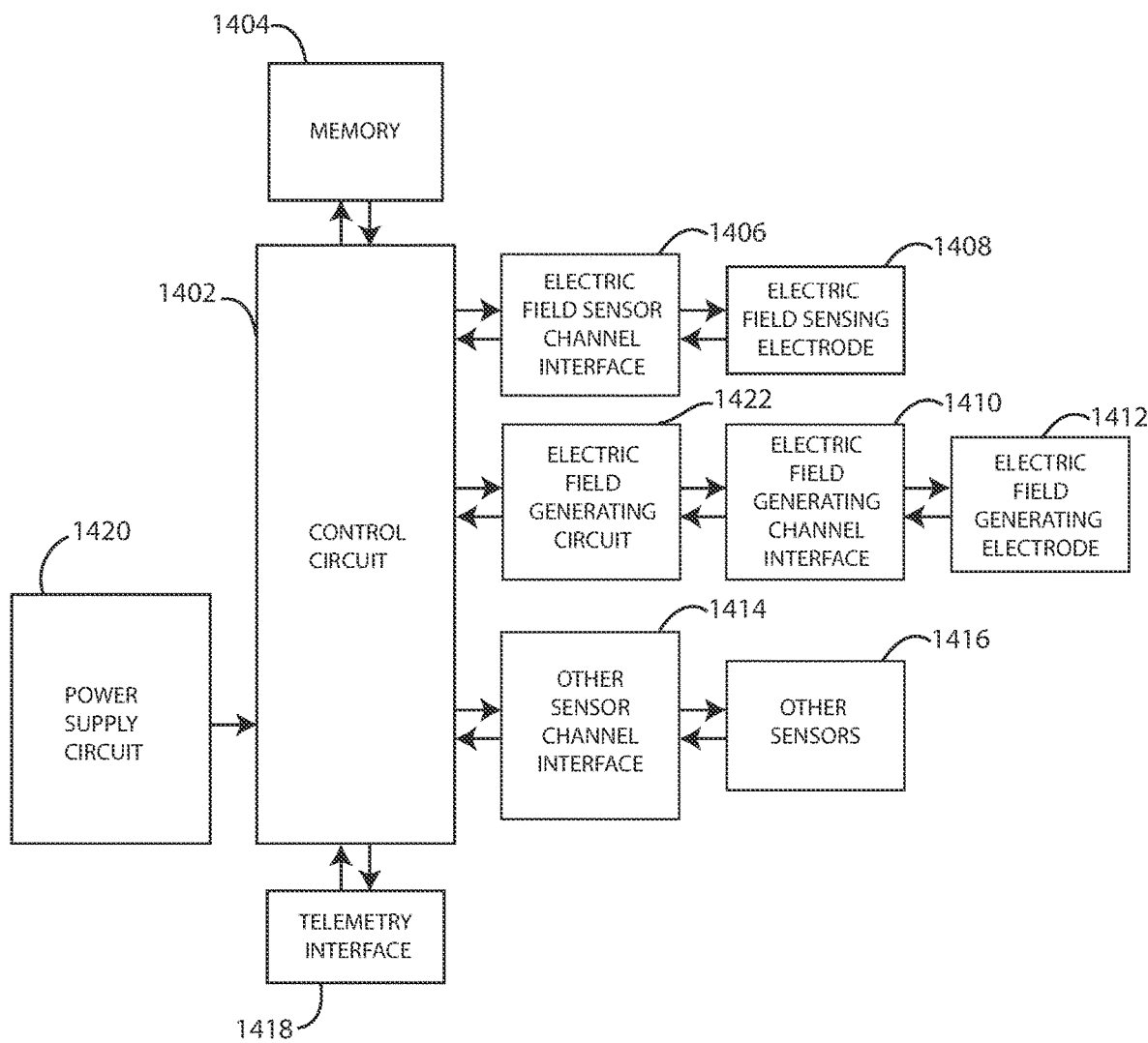
FIG. 14 is a schematic diagram of components of a medical device in accordance with various embodiments herein.

Elements of various embodiments of the medical devices described herein are shown in FIG. 14. However, it will be appreciated that some embodiments can include additional elements beyond those shown in FIG. 14. In addition, some embodiments may lack some elements shown in FIG. 14. The medical devices as embodied herein can gather information through one or more sensing channels and can output information through one or more field generating channels. A microprocessor 1402 can communicate with a memory 1404 via a bidirectional data bus. The memory 1404 can include read only memory (ROM) or random-access memory (RAM) for program storage and RAM for data storage. The microprocessor 1402 can also be connected to a telemetry interface 1418 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. The medical device can include a power supply circuit 1420. In some embodiments, the medical device can include an inductive energy receiver coil interface (not shown) communicatively coupled or attached thereto to facilitate transcutaneous recharging of the medical device.

The medical device can include one or more electric field sensing electrodes 1408 and one or more electric field sensor channel interfaces 1406 that can communicate with a port of microprocessor 1402. The medical device can also include one or more electric field generating circuits 1422, one or more electric field generating electrodes 1412, and one or more electric field generating channel interfaces 1410 that can communicate with a port of microprocessor 1402. The medical device can also include one or more physiological sensors, respiration sensors, or chemical sensors 1416 and one or more physiological/respiration/chemical sensor channel interfaces 1414 that can communicate with a port of microprocessor 1402. The channel interfaces 1406, 1410, and 1414 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the physiological sensors can include sensors that monitor temperature, blood flow, blood pressure, and the like. In some embodiments, the respiration sensors can include sensors that monitor respiration rate, respiration peak amplitude, and the like. In some embodiments, the chemical sensors can measure the quantity of an analyte present in a treatment area about the sensor, including but not limited to analytes such as of blood urea nitrogen, creatinine, fibrin, fibrinogen, immunoglobulins, deoxyribonucleic acids, ribonucleic acids, potassium, sodium, chloride, calcium, magnesium, lithium, hydronium, hydrogen phosphate, bicarbonate, and the like. However, many other analytes are also contemplated herein. Exemplary chemical/analyte sensors are disclosed in commonly owned U.S. Pat. No. 7,809,441 to Kane et al., and which is hereby incorporated by reference in its entirety.

Although the physiological, respiration, or chemical sensors 1416 are shown as part of a medical device in FIG. 14, it is realized that in some embodiments one or more of the physiological, respiration, or chemical sensors could be physically separate from the medical device. In various embodiments, one or more of the physiological, respiration, or chemical sensors can be within another implanted medical device communicatively coupled to a medical device via telemetry interface 1418. In yet other embodiments, one or more of the physiological, respiration, or chemical sensors can be external to the body and coupled to a medical device via telemetry interface 1418.

Methods

Figure 15:
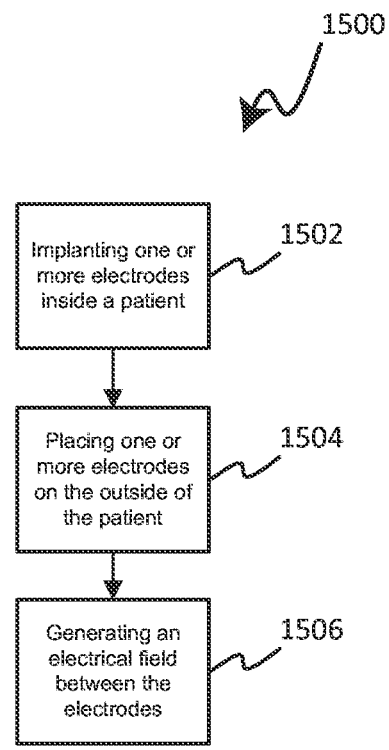
FIG. 15 is a flow chart depicting a method in accordance with various embodiments herein.

In reference now to FIG. 15, a flow chart depicting a method of treating a cancerous tumor is shown. The method 1500 of treating a tumor can include implanting one or more electrodes inside a body of a patient with a tumor, step 1502. The method 1500 can include placing one or more external electrodes on the outside surface of the patient's body, step 1504. The method 1500 can further include generating an electrical field between the electrodes, step 1506. In various embodiments, the electric field can have frequencies within a range of between 10 kHz to 1 MHz.

In some embodiments, the method 1500 can include ceasing or stopping the generation of the electrical field between the electrodes. In some embodiments, the method 1500 can further include moving the one or more electrodes on an outside surface of the patient's body, such as in response to the tumor changing or modifying the treatment. The method 1500 can also include generating an electrical field between at least one pair of electrodes, such as after the one or more external electrodes have been moved. In various embodiments, the electric field can have frequencies within a range of between 10 kHz to 1 MHz.

In various embodiments, the method 1500 can include generating electrical fields between respective electrodes of at least two electrode pairs. In some embodiments, a first electrode pair includes two implanted electrodes and a second electrode pair includes two external electrodes.

Figure 16:
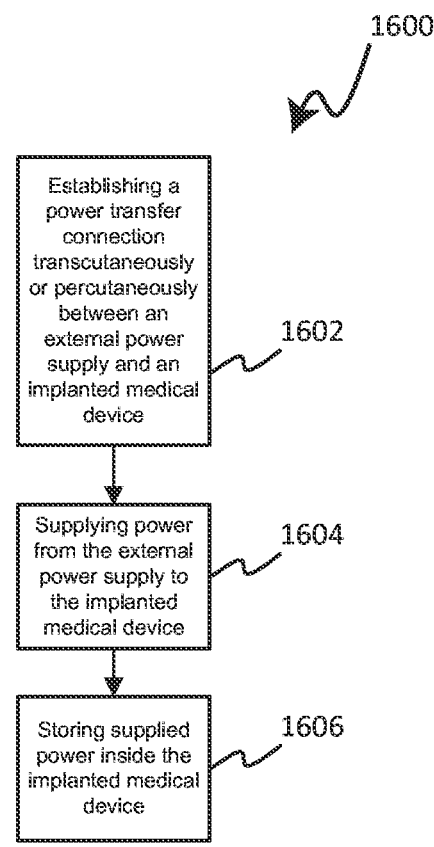
FIG. 16 is a flow chart depicting a method in accordance with various embodiments herein.

Referring now to FIG. 16, a flow chart depicting a method 1600 of providing power to an implanted medical device is shown. The method 1600 for providing power to an implanted medical device can include establishing a power transfer connection, step 1602. In various embodiments, the power transfer connection can be transcutaneously or percutaneous between an external power supply and an implanted medical device.

The method 1600 can include supplying power from the external power supply to the implanted medical device through a power supply probe, step 1604. In some embodiments, the power supplied from the external power supply can be modulated to control electric field generation by the implanted medical device. The method 1600 can include storing the supplied power inside the implanted medical device, step 1606.

Figure 10:
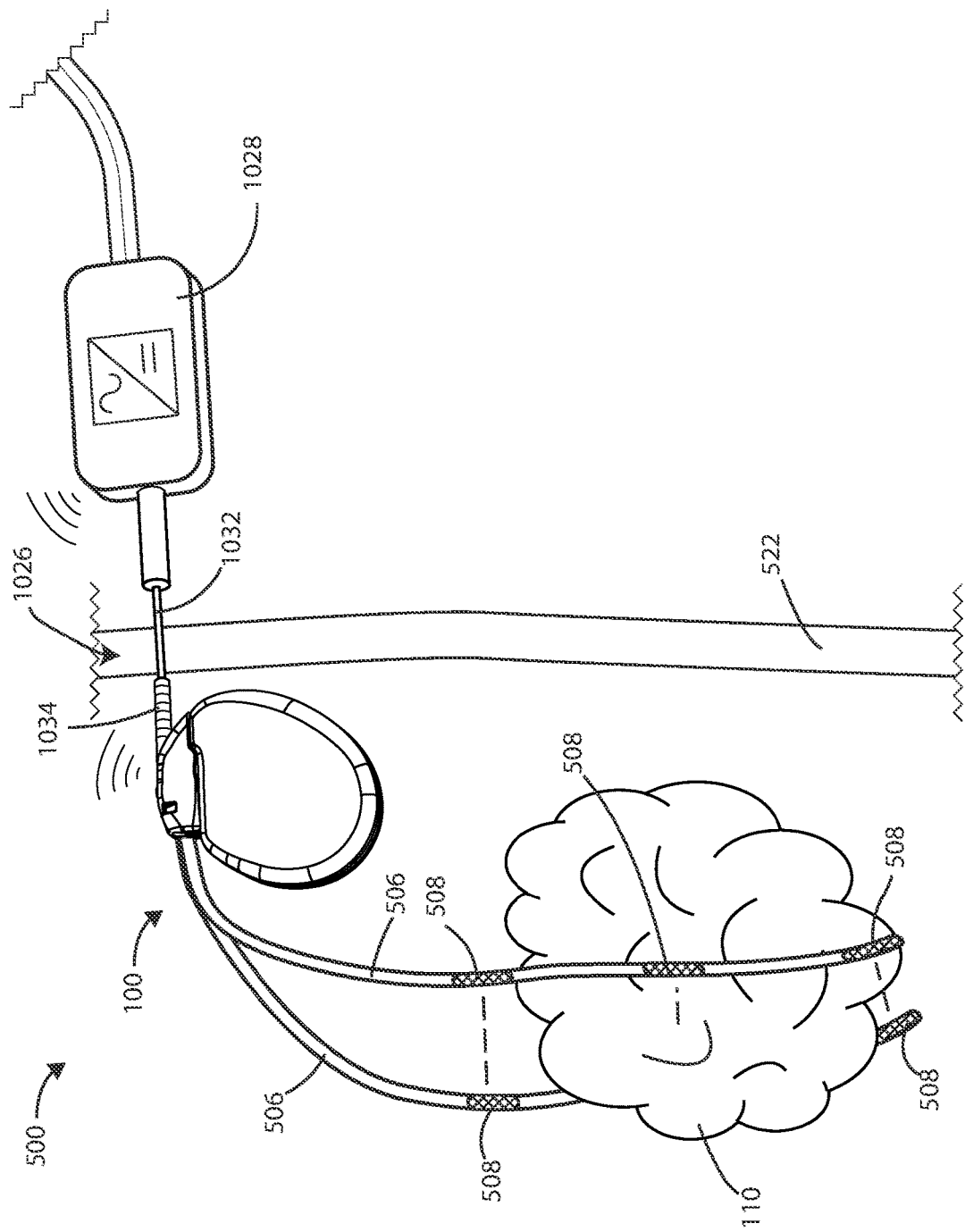
FIG. 10 is a schematic view of a medical device in accordance with various embodiments herein.

In some embodiments, establishing a power transfer connection percutaneously between an external power supply and the implanted medical device can include inserting a power supply probe connected to the external power supply percutaneously into a power connection receiver connected to the implanted medical device, such as shown in FIGS. 10-11. In some embodiments, establishing a power transfer connection transcutaneously between an external power supply and the implanted medical device can include establishing a percutaneous inductive power transfer link, such as shown in FIG. 12. In some embodiments, the implanted medical device can be configured to send a wireless signal for receipt by a secondary device outside of the body. The signal can include information regarding charge level of a battery associated with the implanted medical device.

In various embodiments, the implanted medical device can include at least one electric field generating circuit configured to generate one or more electric fields; control circuitry in communication with the electric field generating circuit, and an interface to electrically connect to two or more electrodes to deliver the electric fields to the site of a cancerous tumor within a patient. In various embodiments, the control circuitry can be configured to control delivery of the one or more electric fields from the at least one electric field generating circuit.

Electrical Stimulation Parameters

In various embodiments, systems or device herein (or components thereof, such as control circuitry) can be configured to direct an electric field generating circuit to deliver an electric field using one or more frequencies selected from a range of between 10 kHz to 1 MHz. In some embodiments, the control circuitry can be configured to direct the electric field generating circuit to deliver an electric field at one or more frequencies selected from a range of between 100 kHz to 500 kHz. In some embodiments, the control circuitry can be configured to direct the electric field generating circuit to deliver an electric field at one or more frequencies selected from a range of between 100 kHz to 300 kHz. In some embodiments, the control circuitry can be configured to direct the electric field generating circuit to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry can be configured to direct the electric field generating circuit to deliver an electric field using currents ranging from 1 mAmp to 1000 mAmp to the site of a cancerous tumor. In some embodiments, the control circuitry can be configured to direct the electric field generating circuit to deliver an electric field using currents ranging from 20 mAmp to 500 mAmp to the site of a cancerous tumor. In some embodiments, the control circuitry can be configured to direct the electric field generating circuit to deliver an electric field using currents ranging from 30 mAmp to 300 mAmp to the site of a cancerous tumor.

In some embodiments, the control circuitry can be configured to direct the electric field generating circuit to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 1320 to deliver an electric field at a current falling within a range, wherein any of the forgoing currents can serve as the lower or upper bound of the range, provided that the lower bound of the range is a value less than the upper bound of the range.

In some embodiments, the control circuitry can be configured to direct the electric field generating circuit to deliver an electric field using voltages ranging from 1 $V_{rms}$ to 50 $V_{rms}$ to the site of a cancerous tumor. In some embodiments, the control circuitry can be configured to direct the electric field generating circuit to deliver an electric field using voltages ranging from 5 $V_{rms}$ to 30 $V_{rms}$ to the site of a cancerous tumor. In some embodiments, the control circuitry can be configured to direct the electric field generating circuit to deliver an electric field using voltages ranging from 10 $V_{rms}$ to 20 $V_{rms}$ to the site of a cancerous tumor.

In some embodiments, the control circuitry can be configured to direct the electric field generating circuit 320 to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit to deliver an electric field using a voltage falling within a range, wherein any of the forgoing voltages can serve as the lower or upper bound of the range, provided that the lower bound of the range is a value less than the upper bound of the range.

In some embodiments, the control circuitry can be configured to direct the electric field generating circuit to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit can deliver an electric field using a frequency falling within a range, wherein any of the foregoing frequencies can serve as the upper or lower bound of the range, provided that the upper bound is greater than the lower bound.

In some embodiments, the control circuitry can be configured to direct the electric field generating circuit to generate one or more applied electric field strengths selected from a range of between 0.25 V/cm to 1000 V/cm. In some embodiments, the control circuitry can be configured to direct the electric field generating circuit to generate one or more applied electric field strengths of greater than 3 V/cm. In some embodiments, the control circuitry can be configured to direct the electric field generating circuit to generate one or more applied electric field strengths selected from a range of between 1 V/cm to 10 V/cm. In some embodiments, the control circuitry can be configured to direct the electric field generating circuit to generate one or more applied electric field strengths selected from a range of between 3 V/cm to 5 V/cm. In other embodiments, the control circuitry can be configured to direct the electric field generating circuit to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit can generate an electric field having a field strength at a treatment site falling within a range, wherein any of the foregoing field strengths can serve as the upper or lower bound of the range, provided that the upper bound is greater than the lower bound.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed, and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device system comprising:
   at least one electric field generating circuit configured to generate two or more electric fields; and
   control circuitry in communication with the electric field generating circuit, the control circuitry configured to control delivery of the two or more electric fields from the at least one electric field generating circuit; and
   four or more electrodes to deliver the electric fields to the site of a cancerous tumor within a patient, wherein at least two electrodes are configured to be non-implanted, and wherein at least two electrodes are configured to be implanted;
   wherein the control circuitry causes the electric field generating circuit to generate two or more electric fields at frequencies selected from a range of between 10 kHz to 1 MHz; and
   an implantable sensor in signal communication with the control circuitry; and
   wherein the electric fields are delivered across at least two vectors, wherein each vector includes both an electrode configured to be implanted and an electrode configured to be non-implanted.

2. The medical device system of claim 1, wherein the implantable sensor is an electric field sensing sensor.

3. The medical device system of claim 1, wherein the implantable sensor is a temperature sensor.

4. The medical device system of claim 1, wherein the implantable sensor is a physiological sensor.

5. The medical device system of claim 1, further comprising an implantable lead.

6. The medical device system of claim 5, wherein the implantable lead is a percutaneous lead.

7. The medical device system of claim 1, comprising at least one implantable housing.

8. The medical device system of claim 1, wherein the electric field strength is greater at the site of the electrode that is configured to be non-implanted than at the site of the electrode that is implantable.

* * * * *